(12) United States Patent
McIver et al.

(10) Patent No.: US 9,341,610 B1
(45) Date of Patent: May 17, 2016

(54) ELECTRICAL ARC TRIGGER SYSTEMS, METHODS, AND APPARATUSES

(71) Applicant: The Boeing Company, Seal Beach, CA (US)

(72) Inventors: Carl Roy McIver, Everett, WA (US); Eddie Kwon, Everett, WA (US)

(73) Assignee: The Boeing Company, Chicago, IL (US)

( * ) Notice: Subject to any disclaimer, the term of this patent is extended or adjusted under 35 U.S.C. 154(b) by 364 days.

(21) Appl. No.: 14/014,053

(22) Filed: Aug. 29, 2013

(51) Int. Cl.

| | | |
|---|---|---|
| *F02P 17/00* | (2006.01) | |
| *G01N 33/22* | (2006.01) | |
| *H01J 37/32* | (2006.01) | |
| *G01R 31/25* | (2006.01) | |
| *G01R 31/24* | (2006.01) | |
| *F02P 15/02* | (2006.01) | |
| *F02P 17/12* | (2006.01) | |
| *F02P 15/04* | (2006.01) | |

(52) U.S. Cl.
CPC .............. *G01N 33/22* (2013.01); *G01R 31/245* (2013.01); *G01R 31/25* (2013.01); *H01J 37/32064* (2013.01); *F02P 15/02* (2013.01); *F02P 15/04* (2013.01); *F02P 17/00* (2013.01); *F02P 17/12* (2013.01)

(58) Field of Classification Search
CPC ........... F02P 15/02; F02P 15/04; F02P 17/00; F02P 17/12; F02P 2017/006; F02P 2017/125; G01R 31/245; G01R 31/25; G01N 33/22; H01J 37/32064
USPC ................... 324/378, 382, 395, 396, 402, 409
See application file for complete search history.

(56) References Cited

U.S. PATENT DOCUMENTS

| | | | |
|---|---|---|---|
| 4,233,835 A | 11/1980 | Dahn | |
| 4,407,849 A | 10/1983 | Haas et al. | |
| 4,589,398 A | 5/1986 | Pate et al. | |
| 5,216,325 A | 6/1993 | Patel et al. | |
| 5,548,461 A * | 8/1996 | James | G01S 7/4052 361/13 |
| 5,663,694 A | 9/1997 | Goebel et al. | |
| 5,754,011 A | 5/1998 | Frus et al. | |
| 6,553,981 B1 | 4/2003 | Suckewer et al. | |
| 6,903,357 B2 | 6/2005 | Robb | |

(Continued)

OTHER PUBLICATIONS

Lux, "Triggered Spark Gaps," http://home.earthlink.net/~jimlux/hv/hvtrigsg.htm, 1997 (revised Jan. 11, 2000 and Mar. 17, 2001), downloaded on Jan. 17, 2014.

(Continued)

*Primary Examiner* — Hoai-An D Nguyen
(74) *Attorney, Agent, or Firm* — Dascenzo Intellectual Property Law, PC

(57) ABSTRACT

Systems, methods, and apparatuses for triggering electrical arcs are disclosed. Such arcs are useful for testing combustible fluids and equipment operating near ignition hazards. In some embodiments, arcs are produced with a defined energy at a defined time with little variation in arc energy. Consistent production of arcs is facilitated by one or more of conditioned electrodes, control and/or reduction of parasitic capacitance, avoidance of corona sources, and non-interfering arc triggers. In some embodiments, electrodes are conditioned by repeated application of conditioning arcs. Conditioned electrodes have relatively physically consistent and chemically consistent tips. In some embodiments, arc triggers are charged particle sources such as light sources operating in cooperation with a target to produce free electrons proximate the electrodes.

22 Claims, 3 Drawing Sheets

(56) References Cited

U.S. PATENT DOCUMENTS

| | | | |
|---|---|---|---|
| 7,748,323 | B2 | 7/2010 | Maeda et al. |
| 8,858,222 | B1* | 10/2014 | Adams ................. F23N 5/20 |
| | | | 431/1 |
| 2002/0112687 | A1 | 8/2002 | Labarge et al. |
| 2003/0047444 | A1* | 3/2003 | Boxman ................. H05H 1/24 |
| | | | 204/192.38 |
| 2007/0058319 | A1 | 3/2007 | Frescaline et al. |
| 2009/0153142 | A1* | 6/2009 | Agneray ................. F02P 3/01 |
| | | | 324/400 |
| 2010/0201370 | A1 | 8/2010 | Coumou et al. |
| 2012/0063054 | A1 | 3/2012 | Burrows et al. |
| 2014/0130619 | A1 | 5/2014 | Mraz et al. |

OTHER PUBLICATIONS

"Standard Test Method for Minimum Ignition Energy and Quenching Distance in Gaseous Mixtures," ASTM International Designation: E 582-04, 2004.

Shepherd et al., "Spark Ignition Energy Measurements in Jet A," Graduate Aeronautical Laboratories, California Institute of Technology, Pasadena, California, May 3, 1999 (revised Jan. 24, 2000).

"Aircraft Fuel System Lightning Protection Design and Qualification Test Procedures Development," Final Report, DOT/FAA/CT-94/74, Sep. 1994.

* cited by examiner

ELECTRICAL ARC TRIGGER SYSTEMS, METHODS, AND APPARATUSES

FIELD

The present disclosure relates to systems, methods, and apparatuses for triggering electrical arcs.

BACKGROUND

In many situations, devices must operate in potentially hazardous conditions, such as where a fuel mixture may be ignited by uncontrolled operating or environmental conditions. For example, vehicles, including aerospace vehicles, typically operate with a fuel that must be maintained in a safe condition during storage and use. The ignition hazard should be minimized even when the vehicle is subject to uncontrolled events such as an accident, electrical malfunction, a lightning strike, or static electrical discharge. Other applications requiring ignition hazard consideration include fuel transport, fuel storage, mining operations, and operations which involve combustible particulate such as sawdust, flour, and grain.

In the aerospace industry, lightning strikes of aircraft are a concern because they could result in electrical arcs and/or heating sufficient to ignite vaporous fuel mixtures. Though lightning passes through metallic aircraft virtually always without resulting harm, manufacturers and regulators are vigilant to the potential for harm. The Federal Aviation Authority (FAA) recognizes that arc energies as low as 200 µJ (microjoules) may be sufficient to cause unwanted ignition of vaporous fuels.

Design of apparatuses exposed to ignition hazards typically involves reducing the likelihood of ignition, containing the ignition hazard, and/or withstanding the ignition hazard. Test systems may facilitate the design by simulating ignition of a combustible fluid in a controlled environment. To initiate ignition of a combustible fluid, test systems may include an arc source, i.e., a source of electric discharge, sometimes referred to as a spark. This discharge may be used to ignite a combustible and/or explosive material (typically gaseous or vaporous), in particular to test a test sample, such as combustible and/or explosive materials (including fuel mixtures), and structures, devices, and/or apparatuses intended to operate near ignition hazards. The arc source may be used to simulate unwanted electrical discharge, to verify that test conditions are proper for ignition, and/or to calibrate the ignition point for a combustible and/or explosive material.

SUMMARY

Controlled electrical arcs may be produced in test systems and/or apparatuses by applying a voltage across an electrode gap and triggering an arc across the electrode gap. The applied voltage may be approximately the same as a breakdown voltage of a medium spanning the electrode gap and/or may be about 0-300 V less than the breakdown voltage. The triggering may include supplying charged particles into the electrode gap while not otherwise interfering with the triggered arc. Supplying may be accomplished with a trigger source, such as a light source in cooperation with a target. Illuminating a target with the appropriate optical power and/or photon energy may cause the target to emit electrons, ions, and/or other charged particles.

Systems and/or apparatuses for producing controlled electrical arcs include at least two electrodes with electrode tips. The electrode tips are spaced apart to delimit an electrode gap. When a sufficiently high voltage is applied across the electrode gap, a medium spanning the electrode gap will break down, causing an electrical arc. The systems and/or apparatuses include a trigger source, such as a light source in cooperation with a target. The trigger source may further include a delivery conduit, such as a fiber optic, which delivers energy to the target. The target may include a portion of one of the electrodes delimiting the electrode gap.

Test systems may include a test chamber, an electrical arc source at least partially enclosed by the test chamber, and a test sample at least partially enclosed by the test chamber. The test chamber may further enclose a combustible fluid.

DESCRIPTION

Figure 1:
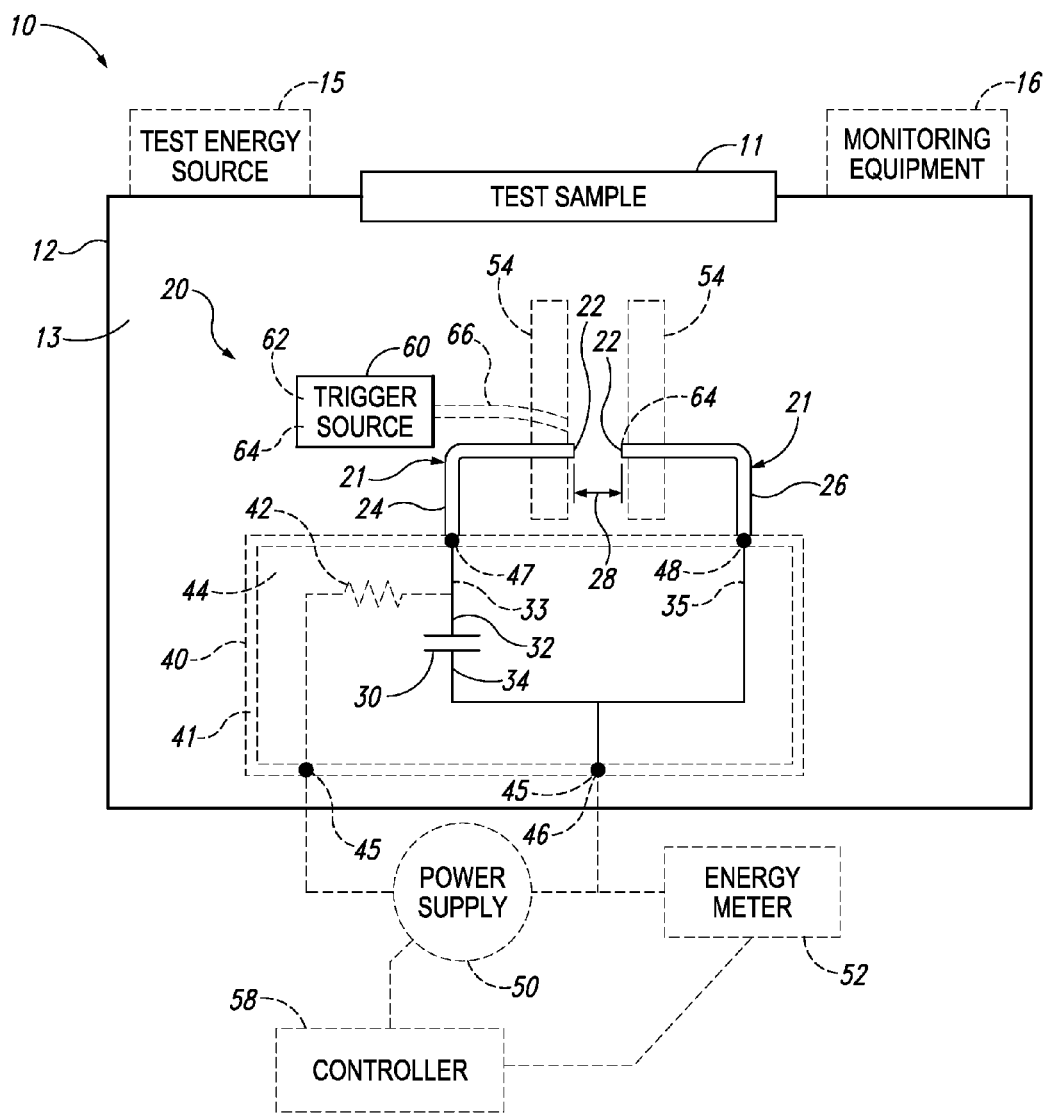
FIG. 1 is a schematic representation of systems and apparatuses according to the present disclosure.

The present disclosure relates to systems, methods, and apparatuses for controlled-energy electrical arcs. FIG. 1 schematically presents systems 10 and apparatuses 20 for controlled-energy electrical arcs. Systems 10 incorporate one or more apparatuses 20, and may be used to test the effect of electrical arcs, or electrical energy discharge, on a test sample 11 potentially exposed to ignition hazards within a test chamber 12.

Systems 10 may be used to test, to calibrate, and/or to verify test samples 11 with respect to controlled ignition hazards. Test samples 11 may include, and may be, one or more of a solid, liquid, and gas. For example, a test sample 11 may be a solid structural member of an aircraft, a liquid fuel, or a fuel vapor-air mixture. Test samples 11 may include, and optionally be, a fuel mixture, an aerospace component, a fuel handling component, a ventilator component, and/or equipment. Illustrative, non-exhaustive examples include an aircraft skin, an aircraft frame, a fuel pump, a fuel tank, mining equipment, ventilator equipment, dust handling equipment, monitoring equipment, and a camera.

The test chamber 12 of a system 10 may enclose all or part of the test sample 11. The test chamber 12 may be a pressure bomb, a sealed chamber, an enclosed space, and/or a partitioned space. Within the test chamber 12, and in contact with at least part of the test sample 11, may be a combustible fluid 13. The combustible fluid 13 may be combustible, flammable, and/or explosive. The presence of the combustible fluid 13 near the test sample 11 allows the test sample 11 to be tested for the ability to ignite the combustible fluid 13 and/or to survive the combustion, explosive or otherwise, of the combustible fluid 13. Typically, the combustible fluid 13 is liquid or gaseous, potentially including a suspension of solid particles and/or liquid droplets. Illustrative, non-exclusive examples of combustible fluids 13 include one or more of air, oxygen, hydrogen, a hydrocarbon, a fuel, a fuel vapor, an oxidant, dust, powder, and particulate.

Systems 10 may include a test energy source 15 to apply energy to the test sample 11 and/or the combustible fluid 13. The energy imparted may simulate use of the test sample 11, and/or may simulate environmental conditions. Illustrative, non-exclusive examples of test energy sources 15 include a lightning simulator, a heater, and an exposed electrical arc.

Systems 10 may include monitoring equipment 16 to observe and/or record conditions during the test. Monitoring equipment 16 may measure one or more of temperature, pressure, electrical power, electrical charge, electrical voltage, electrical properties, light, sound, and chemical properties. Illustrative, non-exclusive examples of monitoring equipment include pressure transducers, pressure indicators, microphones, heat transducers, heat indicators, photodetectors, cameras, electrical power meters, electrostatic voltmeters, oscilloscopes, and current sensors (e.g. Rogowski coils).

Systems 10 incorporate at least one apparatus 20 to create an electrical arc. The system 10 and/or the test conducted using the system 10 may depend upon the actual arc energy and/or the timing of the arc. The arc may be used to ignite the combustible fluid 13 when present, may be used to detect the presence of a combustible fluid 13, may be used to verify the absence of a combustible fluid 13, and/or may be used to detect the composition of a combustible fluid 13.

Apparatuses 20 comprise at least two electrodes 21, a first electrode 24 and a second electrode 26, that are spaced apart to delimit an electrode gap 28 between the tips 22 of the electrodes 21. Electrical arcs may be created across the electrode gap 28 when a sufficient source of electrical energy is connected across the electrodes and when a sufficient voltage is applied across the electrode gap 28. Electrical arcs typically are created by causing any material spanning the electrode gap 28 to dielectrically break down. Arcs may be created in a medium such as a combustible fluid 13 and may be created in conditions other than standard temperature and pressure. The breakdown voltage, or discharge voltage, is dependent upon many factors, including material properties and geometries. For example, the breakdown voltage may be affected by the length of the electrode gap 28, the shape of the electrode tips 22, the material properties of the electrode tips 22, and/or the composition of any material spanning the electrode gap 28.

The breakdown voltage of a material may be characterized by the dielectric strength of the material. In an insulating material, dielectric strength is a measure of the resistance to breakdown. It is the minimum voltage required to cause dielectric breakdown and/or ionization of the material. Dielectric strength is measured in volts per unit thickness. Generally, a higher dielectric strength indicates a better insulator. Many common insulating materials have a dielectric strength between 1 MV/m (megavolt per meter) and 100 MV/m. For example, air and nitrogen have a dielectric strength of about 3 MV/m, while insulating fluids, like mineral oil, have a dielectric strength of about 10-20 MV/m. When operating with an air mixture in an electrode gap 28 of several millimeters, the breakdown voltage that will generate an arc is several thousand volts. Typical electrode gaps 28 are less than 10 mm, less than 8 mm, less than 6 mm, less than 5 mm, less than 4 mm, less than 3 mm, less than 2.5 mm, less than 2 mm, less than 1.5 mm, less than 1 mm, less than 0.5 mm, 0.5-10 mm, or 0.5-3 mm.

To create an arc, electrodes 21 are generally conductive and capable of enduring high voltages. Electrodes 21 may include, or be composed of, a metal or similar conductor such as tungsten, aluminium, stainless steel, copper, brass, nickel, silver, gold, platinum, and/or palladium. Electrodes 21 may be metallic and/or plated with a metal or similar conductor. Electrodes 21 may have a generally wire-like form with a diameter of less than 8 mm, less than 6 mm, less than 5 mm, less than 4 mm, less than 3 mm, less than 2 mm, less than 1.5 mm, less than 1 mm, greater than 1 mm, greater than 1.5 mm, greater than 2 mm, greater than 3 mm, about 1-6 mm, and/or about 1-3 mm. The electrode tips 22 may be substantially planar, beveled, conical, rounded, convex, and/or substantially hemispherical.

Apparatuses 20 to create a controlled-energy electrical arc comprise at least one capacitor 30 with a first terminal 32 electrically connected, optionally via a first lead 33, to the first electrode 24 and a second terminal 34 electrically connected, optionally via a second lead 35, to the second electrode 26. The capacitor 30 may store energy that may be readily discharged across the electrode gap 28 to create an arc. The stored energy of a capacitor is related to the capacitance and the voltage across the capacitor: $E=\frac{1}{2}CV^2$, where E is the energy, C is the capacitance, and V is the voltage. The capacitor 30 is configured to store a defined discharge energy at a defined discharge voltage that may be substantially discharged across the electrode gap 28 in an arc between the electrode tips 22 when electric breakdown occurs across the electrode gap 28.

To store energy sufficient to create an ignition-producing arc, the capacitor 30 may be configured to operate with a high voltage between the first terminal 32 and the second terminal 34. Typical operating voltages, and hence typical defined discharge voltages, are at least 3 kV (kilovolts), at least 4 kV, at least 5 kV, at least 6 kV, at least 7 kV, at least 8 kV, at least 9 kV, at least 10 kV, at least 11 kV, at least 12 kV, 0-10 kV, 0-8 kV, 6-8 kV, less than 15 kV, less than 12 kV, and/or less than 10 kV. The energy stored as a defined discharge energy may be a low energy and may be about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ, 100-250 µJ, and/or less than 1,000 µJ. The capacitor 30 may have a capacitance of about 1 pF (picofarads), about 2 pF, about 4 pF, about 6 pF, about 8 pF, about 10 pF, about 12 pF, about 15 pF, about 20 pF, about 25 pF, about 30 pF, about 50 pF, about 2-10 pF, about 2-15 pF, about 4-20 pF, less than 50 pF, less than 20 pF, or less than 10 pF. The capacitor 30 may be a variable capacitor which may be adjusted between arcs and which may be manually and/or automatically adjusted.

The arc energy may be substantially the same as, greater than, or less than, the defined discharge energy, the energy stored in the capacitor 30. For example, the defined discharge energy may be greater than 50%, greater than 70%, greater than 80%, greater than 90%, greater than 95%, greater than 99%, greater than 100%, or greater than 110% of the arc energy. Where the arc energy is greater than the defined discharge energy, the excess energy may be contributed by outside energy sources e.g., from energy stored in parasitic capacitance and/or from energy contributed by an arc trigger. Where system 10 and/or the apparatus 20 is configured with few to no outside energy sources, the arc energy is dominated by, and may be essentially the same as, the defined discharge energy.

In other electrical arc generating systems and apparatuses, the arc energy may include significant contributions from external sources and/or may not completely discharge the capacitor. For example, all electrical components have parasitic capacitance, i.e., capacitance between the component and another in the system or environment. Parasitic capacitance typically is a few picofarads to a few hundred picofarads. At high voltages, such levels of parasitic capacitance may store several millijoules of energy. Systems 10 and/or apparatuses 20 of the present disclosure may be configured to have low parasitic capacitance and/or non-interfering energy storage from parasitic capacitance. For example, systems 10 and/or apparatuses 20 may have a parasitic capacitance of less than 2 pF, less than 1 pF, less than 0.5 pF, less than 0.2 pF, or less than 0.1 pF. Additionally or alternatively, systems 10 and/or apparatuses 20 may be configured to have a controlled parasitic capacitance, a parasitic capacitance that does not significantly change during utilization of the system 10 and/or apparatus 20. If the net capacitance, the capacitance of the capacitor 30 and the parasitic capacitance, is predictable, the energy stored in capacitance, and hence the energy available for discharge, may be consistent and predictable. The net capacitance of systems 10 and/or apparatuses 20 may be about 1 pF, about 2 pF, about 4 pF, about 6 pF, about 8 pF, about 10 pF, about 12 pF, about 15 pF, about 20 pF, about 25 pF, about 30 pF, about 50 pF, about 2-10 pF, about 2-15 pF, about 4-20 pF, less than 50 pF, less than 20 pF, or less than 10 pF.

Systems 10 and/or apparatuses 20 may comprise an isolation resistor 42 in series with the capacitor 30. The isolation resistor 42 may be in series with a power supply 50, in which case voltage would be applied across the isolation resistor 42 and the capacitor 30. Generally, the isolation resistor 42 has a sufficiently high resistance to electrically isolate the capacitor 30 and the electrodes 21 from any other electrical components, such as power supply 50. Further, the isolation resistor 42 and the capacitor 30 may act as a low pass filter, isolating high frequency arc energy from any other electrical components. Electrical isolation allows for the discharge of the defined discharge energy from the capacitor 30 into the electrode gap 28 with little interference from outside energy sources. The isolation resistor 42 may have a resistance greater than 1 GΩ (gigaohms), greater than 10 GΩ, greater than 50 GΩ, greater than 100 GΩ, greater than 150 GΩ, greater than 200 GΩ, greater than 300 GΩ, or greater than 500 GΩ.

Because a simple electrical system may provide low parasitic capacitance and high isolation from outside influences, apparatuses 20 may comprise a discharge circuit that consists essentially of, and optionally consists of, the capacitor 30, and, when present, the isolation resistor 42. The discharge circuit may include other electrical components but, in its simplest form, does not include additional electrical components. The discharge circuit is electrically coupled to the electrodes 21 and may be electrically coupled to other electrical components, such as a power source 50.

For isolation from outside influences, simplified handling and/or compact packaging, the capacitor 30 may be enclosed in a housing 40. The housing 40 may seal, protect, and/or isolate the capacitor 30, the optional first lead 33, the optional second lead 35, the optional isolation resistor 42, and a portion of each electrode 21, not including the electrode tips 22. The electrodes 21 may be detachable from the housing 40 and if so may be connected to the housing 40 through at least a first electrode connector 47 and a second electrode connector 48. The housing 40 may be fabricated with dimensionally stable materials that are electrically insulating and that generally would not interfere with or be damaged by test conditions in system 10.

To seal, to protect, and/or to isolate the components within the housing, the housing may be composed of a housing material 41. For example, to protect from electrical breakdown, the housing material 41 may have a high dielectric strength of greater than 3 MV/m, greater than 4 MV/m, greater than 5 MV/m, greater than 7 MV/m, greater than 10 MV/m, greater than 15 MV/m, greater than 20 MV/m, about 10 MV/m, about 15 MV/m, or about 20 MV/m. To reduce parasitic capacitance, the housing material 41 may have a low dielectric constant, also called the relative permittivity (a measure of a material's ability to store energy under an applied voltage). The dielectric constant of the housing material 41 may be less than about 10, less than about 5, less than about 3, or less than about 2. For example, the housing may be substantially composed of, and/or may include, PTFE (polytetrafluoroethylene), fluoropolymer, PEEK (polyether ether ketone), polyoxymethylene (Delrin plastic), hard rubber, phenolic resin, polyamide, ceramic, and/or glass.

Additionally or alternatively, to seal, to protect, and/or to isolate the components within the housing 40, the housing 40 may be filled with a fill material 44 and/or may contain a vacuum. The fill material 44 may have a high dielectric strength of greater than 3 MV/m, greater than 4 MV/m, greater than 5 MV/m, greater than 7 MV/m, greater than 10 MV/m, greater than 15 MV/m, greater than 20 MV/m, about 10 MV/m, about 15 MV/m, or about 20 MV/m. The fill material 44 may have a low dielectric constant of less than about 10, less than about 5, less than about 3, or less than about 2. For example, the fill material 44 may include insulating oil, mineral oil, silicone oil, perfluorinated fluid (Fluorinert fluid), silicone resin, polyurethane, epoxy, and/or potting compound.

Use of high dielectric strength materials and/or arc suppression materials may facilitate a compact size for the housing 40. Under high voltage, electrical components may arc between terminals or between components. Arc failures may be reduced by spacing components apart and/or by use of high dielectric strength materials. Hence, with appropriate materials choice and design, the housing 40 may be a compact package. The housing may have a volume of less than 1,000 cm³, less than 500 cm³, less than 200 cm³, or less than 100 cm³. For example, the housing may be about 12 cm×8 cm×10 cm, or about 10 cm×6 cm×4 cm, but other dimensions are within the scope of the present disclosure.

The housing 40 may be configured not to interfere and/or not to interact with systems 10, apparatuses 20, test conditions, and/or arcs in the electrode gap 28. To protect the components within the housing 40 and/or to make the housing 40 durable under test conditions, the housing 40 may be configured to not readily absorb and/or to not readily react with components within systems 10, e.g., moisture, fuels, liquids, gases and/or chemicals. Further, the housing 40 may be poorly electrically conductive and/or not readily combustible. The housing 40 may be one or more of electrically insulating, non-absorbent, non-hygroscopic, inert, non-reactive, non-reactive with hydrocarbon fuels, and non-flammable.

Systems 10 and/or apparatuses 20 may be configured to produce repeatable arcs, with a consistent arc energy. The consistency in arc energy, the reproducibility of an arc by the system 10 and/or apparatus 20, may be due in part to the simple, highly isolated, electrical configurations described above, to optional conditioning of the electrodes 21, and to an optional trigger source 60. Generally systems 10 and/or apparatuses 20 are sufficiently repeatable when arcs may be reproduced under essentially the same conditions with essentially the same energy. For example, systems 10 and/or apparatuses 20 may produce a series of arcs with substantially the same arc energies. The relative standard deviation (the standard deviation divided by the mean) in arc energy may be less than 30%, less than 20%, less than 10%, less than 5%, less than 2%, or less than 1%. Determining the relative standard deviation in arc energy may include determining the arc energy for at least 10 arcs, at least 30 arcs, at least 100 arcs, at least 300 arcs, or at least 1,000 arcs.

The electrode tips 22 may be conditioned to facilitate repeatable arcs within a system 10 and/or an apparatus 20. Conditioning generally results in electrodes 21 with a relatively consistent surface at the electrode tips 22, both in terms of surface features and chemical composition. The conditioned electrodes 21 generally have no dominant microscopic feature that would lead to variability in arc energy and/or breakdown voltage. Microscopic protrusions and/or domains of dielectric material on the electrode tips 22 may influence the local electric field and hence lead to variability of the breakdown voltage and/or arc energy. Conditioned electrode tips 22 may include inhomogeneous surface properties, e.g., protrusions and/or dielectric domains, provided that the surface properties remain stable from arc to arc.

The relatively consistent surfaces of the electrode tips 22 are generally consistent spatially and temporally. The electrode tips 22 may be conditioned by repeatedly electrically arcing the system 10 and/or apparatus 20 until the arc is relatively consistent. Conditioning may involve repeatedly electrically arcing for more than 100, more than 200, more than 300, more than 400, more than 500, more than 1,000, more than 2,000, more than 3,000, more than 4,000, more than 5,000, more than 6,000, more than 7,000, more than 10,000, 100-500, 200-1,000, 1,000-10,000, 2,000-5,000, about 200, about 400, about 2,000, about 3,000, about 4,000, or about 5,000 arcs.

The arc is relatively consistent when an arc parameter and/or a surface parameter is sufficiently reproducible. An arc parameter may include one or more of arc energy, arc voltage, arc duration, and arc power. Sufficiently reproducible arc parameters may have a relative standard deviation of less than 30%, less than 20%, less than 10%, less than 5%, less than 2%, less than 1%, less than 0.5%, less than 0.2%, or less than 0.1%. A surface parameter may include surface roughness and/or chemical composition.

Generally, when the arc energy is repeatable to a desired consistency, the electrode tips 22 are conditioned. The act of electrically arcing imparts some arc energy to the electrode tips 22, potentially causing the electrode tips 22 to be microscopically shaped and reformed. For example, protrusions, which may concentrate the electric field, are preferentially heated by the arc, leading to flow of the protrusion into the local surface plane or 'burning' of the protrusion (e.g., evaporation, sputtering, etc.). Also, contaminants and dielectric surface domains are subjected to at least resistive heating during an arc. Upon repeated electrical arcing, the contaminants and/or domains may be 'burned' off the surface and/or the surface may come to a chemical equilibrium wherein a certain fraction of the surface maintains contaminants and/or dielectric domains.

Ultimately, conditioning of the electrode tips 22 results in properties that do not significantly change when subjected to the energy of a typical arc, i.e., where the arc has an energy of about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ, 100-250 µJ, and/or less than 1,000 µJ. For example, the surface features and chemical composition of the electrode tips 22 are not significantly altered by a typical arc.

The surface features may be characterized by the surface roughness, a measure of the deviation from a smooth surface. One measure of roughness is the average roughness, the average deviation of the actual surface from the local surface plane. Electrode tips 22, when conditioned, may have an average roughness of less than 1 µm, less than 0.5 µm, less than 0.2 µm, less than 0.1 µm, less than 0.05 µm, or less than 0.01 µm. Additionally or alternatively, the surface features, such as roughness, may vary across an electrode tip 22. For example, the roughness may be less towards the axial center of the electrode tip 22 and higher away from the axial center to the electrode tip 22.

Electrode tips 22 are not generally conditioned simply by mechanical abrasion, such as sanding, buffing, and/or polishing. Fine polishing may lead to a microscopically smooth surface but the abrasion typically results in a surface that rapidly reacts with the environment, often forming dielectric coatings and/or surface domains that interfere with consistent arc generation.

Proximate to each electrode 21 may be a flange 54. Flanges 54 may be configured to interact with a flame kernel that forms near the arc. A flame kernel is a nascent flame formed, for example, as a result of an arc in a combustible fluid. The flanges 54 may be configured to encourage a flame kernel to grow. The flanges 54 may delimit a flange gap, optionally a substantially planar parallel gap, that includes the electrode gap 28. Appropriate flange gap spacings to interact with a flame kernel include greater than 1 mm, greater than 2 mm, greater than 3 mm, greater than 4 mm, greater than 5 mm, greater than 6 mm, greater than 7 mm, greater than 8 mm, greater than 10 mm, greater than 12 mm, 2-10 mm, 3-10 mm, 6-12 mm, less than 15 mm, less than 12 mm, less than 10 mm, less than 8 mm, and/or less than 6 mm. In directions transverse to the flange gap spacing, the flanges 54 may be less than 50 mm, less than 25 mm, less than 20 mm, less than 15 mm, less than 12 mm, less than 10 mm, less than 8 mm, less than 6 mm, less than 5 mm, 5-50 mm, 6-25 mm, 6-20 mm, 6-12 mm, greater than 5 mm, greater than 6 mm, greater than 8 mm, greater than 10 mm, greater than 12 mm, and/or greater than 20 mm.

The flanges 54 may be configured not to interfere and/or not to interact with systems 10, apparatuses 20, test conditions, and/or arcs in the electrode gap 28. The flanges 54 may be configured to not readily absorb and/or to not readily react with components within systems 10, e.g., moisture, fuels, liquids, gases and/or chemicals. Further, the flanges 54 may be poorly electrically conductive and/or not readily combustible. The flanges 54 may be one or more of electrically insulating, non-absorbent, non-hygroscopic, inert, non-reactive, non-reactive with hydrocarbon fuels, and non-flammable. The flanges 54 may include, and optionally be composed of, a material with a low dielectric constant, optionally wherein the dielectric constant is less than about 10, less than about 5, or less than about 3. Suitable materials for flanges 54 include PTFE, fluoropolymer, PEEK, polyoxymethylene, hard rubber, phenolic resin, polyamide, ceramic, and/or glass.

Consistency of the system 10 and/or apparatus 20 may be affected by the stochastic nature of the breakdown and arc formation process. When a breakdown voltage is placed across a dielectric, generally the dielectric does not immediately break down. Instead, the dielectric may resist the breakdown until a seed event occurs. Typically, the seed event is the introduction of a charged particle. The charged particle may drift from another location in the dielectric, may be generated by processes in the dielectric, such as cosmic ray interactions, and/or may be supplied by a charged particle source outside the dielectric. One source of charged particles is a corona source, an electrode operated at a sufficiently high voltage to ionize the surrounding medium and create electrons and/or ions. As the processes to create a corona and to create a breakdown are similar, the energy from a corona may be significant relative to a breakdown event. Hence, the use of a corona source may impart significant energy to an arc discharge initiated by the presence of the corona.

Systems 10 and/or apparatuses 20 may include a trigger source 60, or an arc trigger, to initiate, or trigger, an arc across the electrode gap 28 at a defined time and/or a defined voltage. The trigger source 60 may be configured to provide charged particles, e.g., eject electrons via the photoelectric effect, proximate the electrode gap 28 when the electrode gap 28 is held at a voltage near the breakdown voltage in the electrode gap 28. The trigger source 60 may include, be, or consist essentially of, at least one of an ion source, a plasma source, a radioactive source, an electron source, an ionizing energy source, and a light source. The charged particles may be emitted by the trigger source 60 and/or may be created due to energy emitted from the trigger source 60. The charged particles may include electrons, positrons, protons, alpha particles, and/or ions. Energy emissions may include ionizing radiation.

Because any energy near the electrode gap 28 may influence the reproducibility of the arc energy, the trigger source 60 may be configured substantially to not interfere with the arc after arc initiation. Typically, the trigger source 60 contributes little energy to the arc, and alteration of the arc characteristics generally is negligible. For example, a trigger source 60 that provides electrons to the electrode gap 28 by inducing the photoelectric effect in a metal proximate to the electrode gap 28, may inject an insignificant amount of energy into the electrode gap 28 and may not significantly affect the arc characteristics. The trigger source 60 may be configured to contribute less than 10%, less than 5%, less than 2%, less than 1%, less than 0.5%, less than 0.2%, or less than 0.1% to the arc energy. The trigger source 60 may be configured to contribute less than 50 µJ, less than 20 µJ, less than 10 µJ, less than 5 µJ, less than 2 µJ, less than 1 µJ, less than 0.5 µJ, less than 0.2 µJ, or less than 0.1 µJ to the arc energy.

Since coronas may inject significant energy into the electrode gap 28, the trigger source 60 may be essentially corona-free, include no corona sources, and/or be free of corona sources. Coronas may be generated at high voltages, hence the trigger source 60 may operate at lower voltages such as less than 1,000 V, less than 100 V, or less than 10 V.

To facilitate control of the arc initiation process, the trigger source 60 may be configured to be selectively enabled, selectively disabled, and/or regulated. Where the trigger source 60 is electronic, the control may be electronic. Additionally or alternatively, the trigger source 60 may be controlled by mechanical devices such as a shutter and/or a diverter. The trigger source 60 may include a delivery conduit 66 to deliver energy and/or charged particles proximate the electrode gap 28. The delivery conduit 66 may include one or more of an optical system, a fiber optic, a light guide, an electron multiplier, an electron accelerator, an ion accelerator, and an ion optic.

The trigger source 60 may include, or may be essentially composed of, an energy emitter 62 and a target 64 that emits charged particles (e.g., electrons, ions, and/or nuclear particles) upon absorbing energy from the energy emitter 62. The energy emitter 62 and the target 64 are configured to cooperate to produce charged particles. For example, the energy emitter 62 may be configured to emit sufficient energy to ionize the target 64 and/or to photoionize the target 64. Ionization occurs when sufficient energy is applied to a material to generate and/or release a charged particle from the material. The material may be solid, liquid, and/or gaseous. Typically, ionization liberates an electron from a material, resulting in a free electron and/or ion. Photoionization is a type of ionization in which the energy applied is in the form of electromagnetic radiation (radiant energy). For example, one type of photoionization, the photoelectric effect, may cause electrons to be ejected from a metal surface when radiant energy is absorbed by the surface.

Generally, ionization requires energy above a critical threshold of the material, typically the ionization energy (the energy required to generate a free electron and/or create an ion from the material). Photoionization typically requires the photon energy (related to the wavelength) to be greater than the ionization energy. However, in the photoelectric effect, the critical threshold for photoionization of a metallic material may be lower than the ionization energy of an isolated atom from the material. The critical energy threshold for the photoelectric effect of a metallic material is called the work function of the material. The target 64 may have an ionization energy of less than about 14 eV (electron volt), less than about 12 eV, less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, and/or 3.5-6 eV. Additionally or alternatively, the target 64 may have a work function of less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, 4-6 eV, and/or 4-5 eV.

The target 64 may include a metal, such as tungsten, aluminium, stainless steel, copper, brass, nickel, silver, gold, platinum, and/or palladium. The target 64 may be located proximate to the electrode gap 28 and may be a portion of one or more of the electrode tips 22 and/or electrodes 21.

The energy emitter 62 of a trigger source 60 may include, and optionally may be, a light source (a radiant energy source) with sufficient photon energy to produce charged particles from the target. The energy of a photon is related to its wavelength: $E=hc/\lambda$, where E is the energy, h is Planck's constant, c is the speed of light, and $\lambda$ is the wavelength. Planck's constant times the speed of light is about 1,240 eV·nm (electron volt-nanometers). Therefore, photon energies of several electron volts, which may ionize materials or otherwise create charged particles, correspond to wavelengths in the ultraviolet (UV) range, generally about 10-400 nm. Hence, the light source may be a UV light source and/or provide light primarily in the UV range. The light source may emit light with wavelengths of about 10-400 nm, about 80-400 nm, about 80-350 nm, about 80-280 nm, about 80-180 nm, about 200-350 nm, about 200-280 nm, or about 260-280 nm. Wavelengths of about 400-700 nm are considered visible light. An energy emitter 62 which emits significant visible light and/or light of longer wavelengths may interfere with monitoring of the arc, monitoring for combustion, and/or monitoring the system 10 generally. The energy emitter may be configured to emit shorter wavelength light while not substantially emitting longer wavelength light. The energy emitter 62 may be configured to not substantially emit visible light, light of wavelength greater than about 440 nm, greater than about 400 nm, greater than about 350 nm, greater than about 320 nm, or greater than about 280 nm. Additionally or alternatively, the energy emitter 62 may emit photons with an energy greater than or equal to a work function of the target and/or an ionization energy of the target.

Where the trigger source 60 includes a light source as an energy emitter 62, the light source may deliver light to the target 64 and/or the electrode gap 28 via a delivery conduit 66. Thus, the light source may be located distant from the target 64 and/or the electrode gap 28.

The trigger source 60 may be operatively coupled to other components of system 10 and/or apparatus 20. For example, the trigger source 60 may be operatively coupled to test chamber 12, electrode 21, housing 40, and/or flange 54. Where the trigger source 60 includes a delivery conduit 66, the delivery conduit 66 may be operatively coupled to other components of system 10 and/or apparatus 20.

Systems 10 and/or apparatuses 20 may include a power supply 50 to supply energy to the capacitor 30, an energy meter 52 to measure the electrical energy discharged through the electrode gap 28, and/or a controller 58 programmed to control one or more components of the system 10 and/or apparatus 20. The power supply 50 may be configured to apply the defined discharge voltage across the capacitor 30, may be connected to the optional housing 40 through one or more power supply connectors 45, may be adjustable, and may be controlled automatically and/or manually. The energy meter 52 may be, or may include, an electrostatic voltmeter, a current sensor, and/or a Rogowski coil. The energy meter 52 may be connected to the optional housing 40 through one or more energy meter connectors 46. The controller 58 may be programmed to control one or more of the storage of the defined discharge energy in the capacitor 30, the discharge of the defined discharge energy in an arc across the electrode gap 28, the setting of the defined discharge voltage, and the operation of the trigger source 60. The controller 58 may be configured to set the defined discharge voltage to a voltage near a breakdown voltage of a medium within the electrode gap 28 and the set voltage may optionally be about equal to, about 100 V less than, about 200 V less than, about 300 V less than, about 400 V less than, about 0-100 V less than, or about 0-300 V less than the breakdown voltage.

Figure 2:
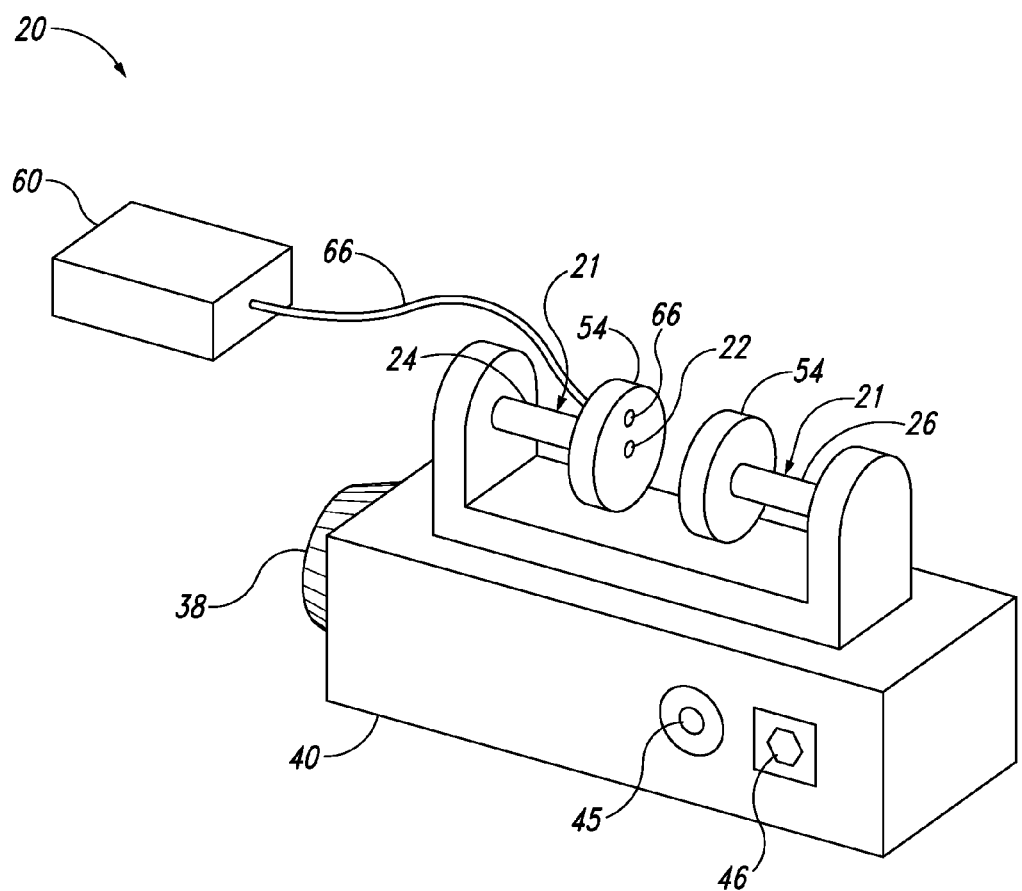
FIG. 2 is a schematic perspective drawing of a non-exclusive, illustrative example of an apparatus according to the present disclosure.

FIG. 2 is a perspective drawing of an illustrative non-exclusive example of apparatus 20. In the example, the capacitor 30 is located within the housing 40 while the electrodes 21 are located above the housing 40. The electrodes 21 include flanges 54 and one flange 54 is operatively coupled to a delivery conduit 66. The apparatus has external connectors, a power supply connector 45 and an energy meter connector 46, to accommodate connection of a power supply 50 and/or an energy meter 52. The housing 40 also includes an adjustment knob 38 that may be used to manually adjust the capacitor 30.

Figure 3:
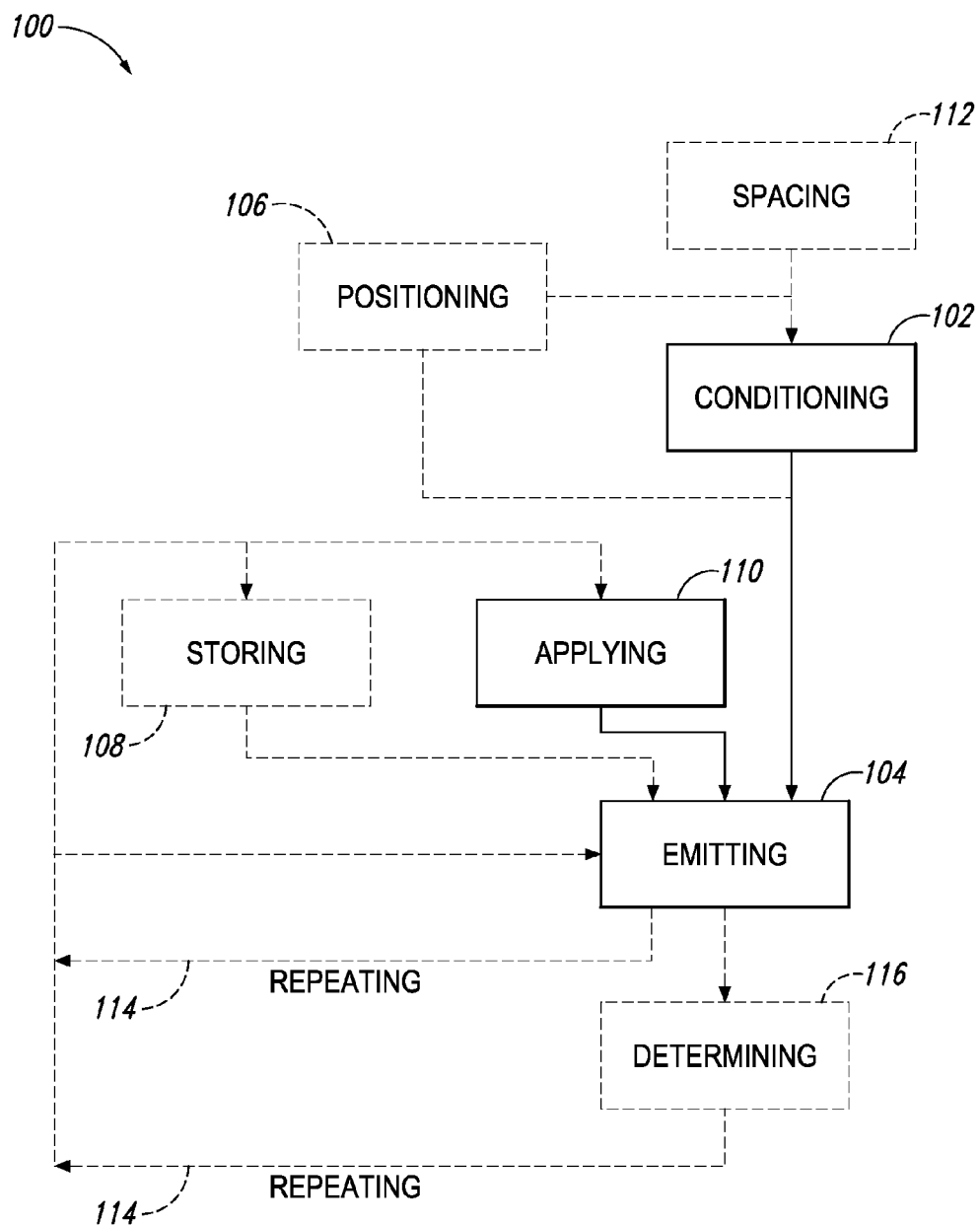
FIG. 3 is a diagram of methods according to the present disclosure.

FIG. 3 is a schematic diagram of methods 100 that may be employed to produce a controlled arc. Methods 100 comprise emitting 104 an arc with an arc energy across an electrode gap delimited by a first electrode tip and a second electrode tip. The systems 10 and apparatuses 20 described above may be useful to perform the methods 100, but other electrical arc systems and apparatuses may be used. The arc energy may be predefined, may be low, and/or may be about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ, 100-250 µJ, and/or less than 1,000 µJ. The emitting 104 may include electrical arcing, discharging the arc and/or triggering the arc. For example, the emitting 104 may include discharging the arc into a combustible fluid spanning the electrode gap. The combustible fluid may be a liquid, a gas, a suspension of solid particles, and/or a suspension of liquid droplets. For example, the combustible fluid may include, or may be, air, oxygen, hydrogen, a hydrocarbon, a fuel, a fuel vapor, an oxidant, dust, powder, and/or particulate.

The emitting 104 may include triggering the arc, optionally at a defined time and/or a defined voltage, for example, by using an arc trigger such as the trigger source 60. Additionally or alternatively, the triggering may include supplying charged particles into the electrode gap and/or regulating a supply of charged particles, for example, using the trigger source 60. The triggering may cause the arc to occur less than 2,000 ms, less than 1,000 ms, less than 500 ms, less than 100 ms, less than 10 ms, less than 1 ms, less than 0.1 ms, less than 0.01 ms, or less than 0.001 ms after the triggering begins. The triggering may be substantially non-interfering with the arc energy. For example, the triggering may contribute less than 10%, less than 5%, less than 2%, less than 1%, less than 0.5%, less than 0.2%, or less than 0.1% to the arc energy. Additionally or alternatively, the triggering may contribute less than 50 µJ, less than 20 µJ, less than 10 µJ, less than 5 µJ, less than 2 µJ less than 1 µJ, less than 0.5 µJ, less than 0.2 µJ, or less than 0.1 µJ to the arc energy. The triggering may be corona-free and/or may not include using a corona source. Generally, emitting 104 may be corona-free and/or may be in the absence of corona sources. Discharging may include stabilizing the arc voltage and/or the arc energy, e.g. by use of conditioned electrodes. Such stabilizing may be in the absence of corona sources.

The supplying charged particles and/or regulating a supply of charged particles may include illuminating a target proximate to the electrode gap. The target may include, or may be composed of, metal such as tungsten, aluminium, stainless steel, copper, brass, nickel, silver, gold, platinum, and/or palladium. The target may be the first electrode tip, the second electrode tip, and/or a portion of one or both of the electrodes. The illuminating may include transmitting light to the target and/or the electrode gap, optionally using a delivery conduit such as an optical system, a fiber optic, and/or a light guide. The light may be essentially UV light and/or may include little to no visible light. For example, the light may consist essentially of wavelengths of about 10-400 nm, about 80-400 nm, about 80-350 nm, about 80-280 nm, about 80-180 nm, about 200-350 nm, about 200-280 nm, or about 260-280 nm. Illuminating may include transmitting light of shorter wavelengths while not substantially transmitting light of longer wavelengths. For example, the light may consist essentially of wavelengths less than about 440 nm, less than about 400 nm, less than about 350 nm, less than about 320 nm, or less than about 280 nm. Transmitting visible and/or longer wavelength light to the electrode gap may interfere with monitoring of the arc, monitoring for combustion in the gap, and/or monitoring the system generally.

The illuminating may include transmitting photons with an energy greater than or equal to a work function of the target and/or a photoionization energy of the target. The target may have a work function less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, 4-6 eV, and/or 4-5 eV. The target may have a photoionization energy of less than about 14 eV, less than about 12 eV, less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, and/or 3.5-6 eV.

Methods 100 may comprise emitting 104 after one or more of positioning 106 the electrodes to delimit the electrode gap, storing 108 stored energy in a capacitor, and applying 110 an electrode voltage across the electrode gap.

Positioning 106 may include delimiting the electrode gap at less than 10 mm, less than 8 mm, less than 6 mm, less than 5 mm, less than 4 mm, less than 3 mm, less than 2.5 mm, less than 2 mm, less than 1.5 mm, less than 1 mm, less than 0.5 mm, 0.5-10 mm, or 0.5-3 mm. Additionally or alternatively, emitting 104 may include emitting an arc across an electrode gap of this distance.

Storing 108 may include storing the arc energy in a capacitor, and/or storing energy to be discharged across the electrode gap. The stored energy may be substantially the same as the arc energy and/or may be greater than 50%, greater than 70%, greater than 80%, greater than 90%, greater than 95%, greater than 99%, greater than 100%, or greater than 110% of the arc energy.

Applying 110 may include applying an electrode voltage which is a high voltage. The electrode voltage may be sufficient to cause dielectric breakdown of any medium spanning the electrode gap. For example, the voltage may be at least 3 kV, at least 4 kV, at least 5 kV, at least 6 kV, at least 7 kV, at least 8 kV, at least 9 kV, at least 10 kV, at least 11 kV, at least 12 kV, less than 15 kV, less than 12 kV, and/or less than 10 kV. Additionally or alternatively, the applying 110 may include setting the electrode voltage near a breakdown voltage of a medium spanning the electrode gap. The electrode voltage may be set to about equal to, about 100 V less than, about 200 V less than, about 300 V less than, about 400 V less than, about 0-100 V less than, or about 0-300 V less than the breakdown voltage.

Methods 100 may comprise determining 116 whether combustion occurred in response to the emitting 104. Determining 116 may include observing, monitoring, measuring, and/or recording one or more system parameters such as electrical power, electrical energy, pressure, temperature, sound level, light level, gas density, gas concentration, and chemical composition. Combustion typically creates at least a flame kernel that consumes at least part of the combustible material. The combustion may generate light, heat, pressure differences and chemical products (such as water and carbon oxides). Determining may include using monitoring equipment, such as monitoring equipment 16.

Methods 100 may comprise repeating 114 the emitting 104. The repeating 114 may include repeating the optional storing 108, the optional applying 110, and/or the optional determining 116. The repeating 114 may produce arcs with a consistent arc energy. For example, the arc energies from the repeated arcs may be substantially the same and/or may have a relative standard deviation that is less than 30%, less than 20%, less than 10%, less than 5%, less than 2%, or less than 1%.

Methods 100 may comprise conditioning 102 the first electrode tip and the second electrode tip before the emitting 104. The conditioning 102 prepares the electrode tips to produce a consistent arc energy upon each emitting 104. The conditioning 102 may include producing a consistent roughness and a consistent surface chemical composition on each of the first electrode tip and the second electrode tip.

Conditioning 102 may include repeatedly applying a conditioning arc between the first electrode tip and the second electrode tip until at least one of an arc parameter and a surface parameter is relatively consistent (as discussed above). Conditioning 102 may include repeatedly electrically arcing for more than 100, more than 200, more than 300, more than 400, more than 500, more than 1,000, more than 2,000, more than 3,000, more than 4,000, more than 5,000, more than 6,000, more than 7,000, more than 10,000, 100-500, 200-1,000, 1,000-10,000, 2,000-5,000, about 200, about 400, about 2,000, about 3,000, about 4,000, or about 5,000 arcs.

Conditioning 102 may include spacing apart 112 the electrode tips prior to applying a conditioning arc. The electrode tip spacing may delimit an electrode gap for conditioning 102, at a conditioning distance, that may be the same as, or different from, the electrode gap for emitting 104. For example, the conditioning distance may be less than 10 mm, less than 8 mm, less than 6 mm, less than 5 mm, less than 4 mm, less than 3 mm, less than 2.5 mm, less than 2 mm, less than 1.5 mm, less than 1 mm, and/or less than 0.5 mm. The electrode tips may be spaced apart 112 in a conditioning surrounding which may be a vacuum or a gaseous medium. Generally, the conditioning surrounding is generally non-combustible and/or inert, e.g., air and/or an inert gas.

The conditioning arcs may have energies about the same as, or different from, an arc from emitting 104. For example, the conditioning arcs may have low energies and/or energies of about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ, 100-250 µJ, and/or less than 1,000 µJ.

The methods 100 may be used to operate a test system and/or test apparatus, optionally one of the systems 10 and the apparatuses 20. The methods may be used to test a test sample, to calibrate a test system, and/or to validate a test condition. The testing, calibrating, and/or validating may include one or more of simulating a lightning strike, initiating combustion of a fuel, applying an electrical arc, qualifying an aerospace component, qualifying an aircraft structural member, qualifying a fuel handling component, qualifying a ventilator component, and qualifying monitoring equipment.

Illustrative, non-exclusive examples of inventive subject matter according to the present disclosure are described in the following enumerated paragraphs:

A1. A controlled-energy electrical arc source comprising:
a first electrode with a tip having a consistent roughness and a consistent surface chemical composition;
a second electrode with a tip having a consistent roughness and a consistent surface chemical composition, wherein the tip of the first electrode and the tip of the second electrode are spaced apart to delimit an electrode gap; and
a capacitor to store a defined discharge energy at a defined discharge voltage, wherein the capacitor has a first terminal electrically connected to the first electrode and a second terminal electrically connected to the second electrode.

A2. The controlled-energy electrical arc source of paragraph A1, wherein the tip of the first electrode and the tip of the second electrode each independently have an average roughness of less than 1 µm, less than 0.5 µm, less than 0.2 µm, less than 0.1 µm, less than 0.05 µm, or less than 0.01 µm.

A3. The controlled-energy electrical arc source of any of paragraphs A1-A2, wherein the tip of the first electrode and the tip of the second electrode are configured such that an arc across the electrode gap does not significantly alter the roughness of the tip of the first electrode and the roughness of the tip of the second electrode, optionally wherein the arc has an energy of about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ, 100-250 µJ, and/or less than 1,000 µJ.

A4. The controlled-energy electrical arc source of any of paragraphs A1-A3, wherein the tip of the first electrode and the tip of the second electrode are configured such that an arc across the electrode gap does not significantly alter the surface chemical composition of the tip of the first electrode and the surface chemical composition of the tip of the second electrode, optionally wherein the arc has an energy of about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ, 100-250 µJ, and/or less than 1,000 µJ.

A5. The controlled-energy electrical arc source of any of paragraphs A1-A4, wherein the first electrode and/or the second electrode includes one or more of metal, tungsten, aluminium, stainless steel, copper, brass, nickel, silver, gold, platinum, and palladium.

A6. The controlled-energy electrical arc source of any of paragraphs A1-A5, wherein the first electrode and/or the second electrode has a diameter less than 8 mm, less than 6 mm, less than 5 mm, less than 4 mm, less than 3 mm, less than 2 mm, less than 1.5 mm, less than 1 mm, greater than 1 mm, greater than 1.5 mm, greater than 2 mm, greater than 3 mm, about 1-6 mm, and/or about 1-3 mm.

A7. The controlled-energy electrical arc source of any of paragraphs A1-A6, wherein the tip of the first electrode and/or the tip of the second electrode is rounded, convex, or substantially hemispherical.

A8. The controlled-energy electrical arc source of any of paragraphs A1-A7, wherein the electrode gap is less than 10 mm, less than 8 mm, less than 6 mm, less than 5 mm, less than 4 mm, less than 3 mm, less than 2.5 mm, less than 2 mm, less than 1.5 mm, less than 1 mm, less than 0.5 mm, 0.5-10 mm, or 0.5-3 mm.

A9. The controlled-energy electrical arc source of any of paragraphs A1-A8, wherein the first electrode and the second electrode are configured to produce an arc in a combustible fluid spanning the electrode gap, optionally wherein the combustible fluid includes at least one of a liquid, a gas, a suspension of solid particles, and a suspension of liquid droplets, and optionally wherein the combustible fluid is air, and/or includes one or more of air, oxygen, hydrogen, a hydrocarbon, a fuel, a fuel vapor, an oxidant, dust, powder, and particulate.

A9.1. The controlled-energy electrical arc source of paragraph A9, wherein the arc has an arc energy substantially the same as the defined discharge energy, optionally wherein the defined discharge energy is greater than 50%, greater than 70%, greater than 80%, greater than 90%, greater than 95%, greater than 99%, greater than 100%, or greater than 110% of the arc energy.

A10. The controlled-energy electrical arc source of any of paragraphs A1-A9.1, wherein the tip of the first electrode and the tip of the second electrode are configured to produce a series of arcs with substantially the same arc energies, optionally wherein a relative standard deviation in arc energy is less than 30%, less than 20%, less than 10%, less than 5%, less than 2%, or less than 1%.

A11. The controlled-energy electrical arc source of any of paragraphs A1-A10, wherein the capacitor is a variable capacitor, optionally wherein the capacitor is an automatically controlled variable capacitor or is a manually controlled variable capacitor.

A12. The controlled-energy electrical arc source of any of paragraphs A1-A11, wherein the capacitor is about 1 pF, about 2 pF, about 4 pF, about 6 pF, about 8 pF, about 10 pF, about 12 pF, about 15 pF, about 20 pF, about 25 pF, about 30 pF, about 50 pF, about 2-10 pF, about 2-15 pF, about 4-20 pF, less than 50 pF, less than 20 pF, or less than 10 pF.

A13. The controlled-energy electrical arc source of any of paragraphs A1-A12, wherein the controlled-energy electrical arc source has a parasitic capacitance of less than 2 pF, less than 1 pF, less than 0.5 pF, less than 0.2 pF, or less than 0.1 pF.

A14. The controlled-energy electrical arc source of any of paragraphs A1-A13, wherein the controlled-energy electrical arc source has a net capacitance of about 1 pF, about 2 pF, about 4 pF, about 6 pF, about 8 pF, about 10 pF, about 12 pF, about 15 pF, about 20 pF, about 25 pF, about 30 pF, about 50 pF, about 2-10 pF, about 2-15 pF, about 4-20 pF, less than 50 pF, less than 20 pF, or less than 10 pF.

A15. The controlled-energy electrical arc source of any of paragraphs A1-A14, wherein the defined discharge energy is about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ, 100-250 µJ, and/or less than 1,000 µJ.

A16. The controlled-energy electrical arc source of any of paragraphs A1-A15, wherein the defined discharge voltage is at least 3 kV, at least 4 kV, at least 5 kV, at least 6 kV, at least 7 kV, at least 8 kV, at least 9 kV, at least 10 kV, at least 11 kV, at least 12 kV, 6-8 kV, less than 15 kV, less than 12 kV, and/or less than 10 kV.

A17. The controlled-energy electrical arc source of any of paragraphs A1-A16, further comprising:

a housing enclosing the capacitor and a first lead to the first electrode and a second lead to the second electrode, optionally wherein the housing is filled with a fill material with a high dielectric strength, optionally wherein the high dielectric strength is greater than 3 MV/m, greater than 4 MV/m, greater than 5 MV/m, greater than 7 MV/m, greater than 10 MV/m, greater than 15 MV/m, greater than 20 MV/m, about 10 MV/m, about 15 MV/m, or about 20 MV/m.

A17.1. The controlled-energy electrical arc source of paragraph A17, wherein the housing is one or more of electrically insulating, non-absorbent, non-hygroscopic, inert, non-reactive, non-reactive with hydrocarbon fuels, and non-flammable.

A17.2. The controlled-energy electrical arc source of any of paragraphs A17-A17.1, wherein the housing includes, or is composed of, a housing material with a low dielectric constant, optionally wherein the dielectric constant is less than about 10, less than about 5, less than about 3, or less than about 2.

A17.3. The controlled-energy electrical arc source of any of paragraphs A17-A17.2, wherein the housing includes one or more of PTFE, fluoropolymer, PEEK, polyoxymethylene, hard rubber, phenolic resin, polyamide, ceramic, and glass.

A17.4. The controlled-energy electrical arc source of any of paragraphs A17-A17.3, wherein the housing has a volume less than 1,000 cm$^3$, less than 500 cm$^3$, less than 200 cm$^3$, or less than 100 cm$^3$.

A17.5. The controlled-energy electrical arc source of any of paragraphs A17-A17.4, wherein the fill material includes one or more of insulating oil, mineral oil, silicone oil, perfluorinated fluid, silicone resin, polyurethane, epoxy, and potting compound.

A18. The controlled-energy electrical arc source of any of paragraphs A1-A17.5, further comprising:

an isolation resistor in series with the capacitor, optionally wherein the isolation resistor is greater than 1 GΩ, greater than 10 GΩ, greater than 50 GΩ, greater than 100 GΩ, greater than 150 GΩ, greater than 200 GΩ, greater than 300 GΩ, or greater than 500 GΩ.

A19. The controlled-energy electrical arc source of any of paragraphs A1-A18, further comprising:

a power supply to supply energy to the capacitor, optionally wherein the power supply is configured to apply the defined discharge voltage across the capacitor.

A19.1. The controlled-energy electrical arc source of paragraph A19, wherein the power supply is configured to apply an adjustable voltage across the capacitor, optionally wherein the adjustable voltage is between 0-10 kV, 0-8 kV, or 6-8 kV.

A20. The controlled-energy electrical arc source of any of paragraphs A1-A19.1, further comprising:

an energy meter to measure the electrical energy discharged through the electrode gap, optionally wherein the energy meter is, or includes, an electrostatic voltmeter, a current sensor, and/or a Rogowski coil.

A21. The controlled-energy electrical arc source of any of paragraphs A1-A20, further comprising:

at least two flanges to allow a flame kernel to grow, wherein a flange is proximate the first electrode and another flange is proximate the second electrode, optionally wherein the at least two flanges delimit a flange gap that includes the electrode gap.

A21.1. The controlled-energy electrical arc source of paragraph A21, wherein the at least two flanges are one or more of electrically insulating, non-absorbent, non-hygroscopic, inert, non-reactive, non-reactive with hydrocarbon fuels, and non-flammable.

A21.2. The controlled-energy electrical arc source of any of paragraphs A21-A21.1, wherein the at least two flanges include, or are composed of, a flange material with a low dielectric constant, optionally wherein the dielectric constant is less than about 10, less than about 5, or less than about 3.

A21.3. The controlled-energy electrical arc source of any of paragraphs A21-A21.2, wherein each flange independently includes one or more of PTFE, fluoropolymer, PEEK, polyoxymethylene, hard rubber, phenolic resin, polyamide, ceramic, and glass.

A21.4. The controlled-energy electrical arc source of any of paragraphs A21-A21.3, wherein a maximum lateral dimension of one or more of the at least two flanges is less than 50 mm, less than 25 mm, less than 20 mm, less than 15 mm, less than 12 mm, less than 10 mm, less than 8 mm, less than 6 mm, less than 5 mm, 5-50 mm, 6-25 mm, 6-20 mm, 6-12 mm, greater than 5 mm, greater than 6 mm, greater than 8 mm, greater than 10 mm, greater than 12 mm, and/or greater than 20 mm.

A21.5. The controlled-energy electrical arc source of any of paragraphs A21-A21.4, wherein flange gap is a substantially planar parallel gap, and optionally is greater than 1 mm, greater than 2 mm, greater than 3 mm, greater than 4 mm, greater than 5 mm, greater than 6 mm, greater than 7 mm, greater than 8 mm, greater than 10 mm, greater than 12 mm, 2-10 mm, 3-10 mm, 6-12 mm, less than 15 mm, less than 12 mm, less than 10 mm, less than 8 mm, and/or less than 6 mm.

A22. The controlled-energy electrical arc source of any of paragraphs A1-A21.5, further comprising:
an arc trigger to initiate an arc with an arc energy across the electrode gap, optionally wherein the arc trigger is configured to provide charged particles proximate to the electrode gap.

A22.1. The controlled-energy electrical arc source of paragraph A22, wherein the arc trigger includes, is, or consists essentially of, at least one of an ion source, a plasma source, a radioactive source, an electron source, an ionizing energy source, and a light source.

A22.2. The controlled-energy electrical arc source of any of paragraphs A22-A22.1, wherein the arc trigger is configured to operate at less than 1,000 V, less than 100 V, or less than 10 V.

A22.3. The controlled-energy electrical arc source of any of paragraphs A22-A22.2, wherein the arc trigger does not include a corona generator and/or is free of a corona source.

A22.4. The controlled-energy electrical arc source of any of paragraphs A22-A22.3, wherein the arc trigger is configured to emit one or more of electrons, positrons, protons, alpha particles, ions, and ionizing radiation.

A22.5. The controlled-energy electrical arc source of any of paragraphs A22-A22.4, wherein the arc trigger is configured to be selectively enabled, selectively disabled, and/or regulated.

A22.6. The controlled-energy electrical arc source of any of paragraphs A22-A22.5, wherein the arc trigger is configured to initiate the arc at a defined time and/or a defined voltage.

A22.7. The controlled-energy electrical arc source of any of paragraphs A22-A22.6, wherein the arc trigger is configured to contribute less than 10%, less than 5%, less than 2%, less than 1%, less than 0.5%, less than 0.2%, or less than 0.1% to the arc energy, and optionally wherein the arc trigger is configured to contribute less than 50 µJ, less than 20 µJ, less than 10 µJ, less than 5 µJ, less than 2 µJ, less than 1 µJ, less than 0.5 µJ, less than 0.2 µJ, or less than 0.1 µJ to the arc energy.

A22.8. The controlled-energy electrical arc source of any of paragraphs A22-A22.7, wherein the arc trigger includes a delivery conduit to deliver energy and/or charged particles proximate the electrode gap, optionally wherein the delivery conduit includes one or more of an optical system, a fiber optic, a light guide, an electron multiplier, an electron accelerator, an ion accelerator, and an ion optic, and optionally, when dependent from paragraph A20, wherein the delivery conduit is operatively coupled to at least one of the at least two flanges.

A22.9. The controlled-energy electrical arc source of any of paragraphs A22-A22.8, wherein the arc trigger includes an energy emitter and a target that emits charged particles upon absorbing energy from the energy emitter.

A22.9.1. The controlled-energy electrical arc source of paragraph A22.9, wherein the energy emitter is configured to emit sufficient energy to ionize the target, optionally to photoionize the target.

A22.9.2. The controlled-energy electrical arc source of any of paragraphs A22.9-A22.9.1, wherein the energy emitter is configured to emit sufficient energy to eject electrons from the target.

A22.9.3. The controlled-energy electrical arc source of any of paragraphs A22.9-A22.9.2, wherein the target has a work function less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, 4-6 eV, or 4-5 eV.

A22.9.4. The controlled-energy electrical arc source of any of paragraphs A22.9-A22.9.3, wherein the target has an ionization energy of less than about 14 eV, less than about 12 eV, less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, or 3.5-6 eV.

A22.9.5. The controlled-energy electrical arc source of any of paragraphs A22.9-A22.9.4, wherein the energy emitter includes, optionally is, a light source or a UV light source; optionally wherein light emitted includes wavelengths of about 10-400 nm, about 80-400 nm, about 80-350 nm, about 80-280 nm, about 80-180 nm, about 200-350 nm, about 200-280 nm, or about 260-280 nm; and optionally wherein the source does not substantially emit visible light, light of wavelength greater than about 440 nm, greater than about 400 nm, greater than about 350 nm, greater than about 320 nm, or greater than about 280 nm.

A22.9.5.1. The controlled-energy electrical arc source of paragraph A22.9.5, wherein the energy emitter emits photons with a photon energy greater than or equal to a work function of the target.

A22.9.5.2. The controlled-energy electrical arc source of any of paragraphs A22.9.5-A22.9.5.1, wherein the energy emitter emits photons with a photon energy greater than or equal to a photoionization energy of the target.

A22.9.6. The controlled-energy electrical arc source of any of paragraphs A22.9-A22.9.5.2, wherein the target includes one or more of a metal, tungsten, aluminium, stainless steel, copper, brass, nickel, silver, gold, platinum, and palladium.

A22.9.7. The controlled-energy electrical arc source of any of paragraphs A22.9-A22.9.6, wherein the target is proximate to the electrode gap.

A22.9.8. The controlled-energy electrical arc source of any of paragraphs A22.9-A22.9.7, wherein the target includes, optionally is, one or more of a portion of the first electrode, a portion of the second electrode, the tip of the first electrode, and the tip of the second electrode.

A23. The controlled-energy electrical arc source of any of paragraphs A1-A22.9.8, further comprising:

a controller programmed to control one or more of the storage of the defined discharge energy in the capacitor, the discharge of the defined discharge energy in an arc across the electrode gap, the setting of the defined discharge voltage, and, when dependent from paragraph A22, the operation of the arc trigger.

A24. The controlled-energy electrical arc source of any of paragraphs A1-A23, further comprising:

a discharge circuit consisting essentially of, optionally consisting of, the capacitor, and, when dependent from paragraph A18, the isolation resistor.

A25. A test system, optionally an aerospace component test system, comprising:

a test chamber;

the controlled-energy electrical arc source of any of paragraphs A1-A24, at least partially enclosed by the test chamber; and a test sample at least partially enclosed by the test chamber.

A25.1. The test system of paragraph A25, further comprising:

an energy source to apply energy to the test sample, optionally wherein the energy source includes, optionally is, one or more of a lightning simulator, a heater, and an exposed electrical arc.

A25.2. The test system of any of paragraphs A25-A25.1, further comprising:

a combustible fluid enclosed by the test chamber, optionally wherein the combustible fluid includes at least one of a liquid, a gas, a suspension of solid particles, and a suspension of liquid droplets, and optionally wherein the combustible fluid is air, and/or includes one or more of air, oxygen, hydrogen, a hydrocarbon, a fuel, a fuel vapor, an oxidant, dust, powder, and particulate.

A25.3. The test system of any of paragraphs A25-A25.2, further comprising:

monitoring equipment, optionally wherein the monitoring equipment includes, optionally is, one or more of a pressure transducer, a pressure indicator, a microphone, a heat transducer, a heat indicator, a photodetector, a camera, an electrical power meter, an electrostatic voltmeter, an oscilloscope, a current sensor, and a Rogowski coil.

A25.4. The test system of any of paragraphs A25-A25.3, wherein the test sample is at least partially solid, liquid and/or gaseous.

A25.5. The test system of any of paragraphs A25-A25.4, wherein the test sample includes, optionally is, a fuel mixture, an aerospace component, an aircraft structural member, a fuel handling component, a ventilator component, and/or equipment.

A26. A fuel mixture calibrated using the controlled-energy electrical arc source of any of paragraphs A1-A24 and/or the test system of any of paragraphs A25-A25.5.

B1. A method of generating a controlled electrical arc, comprising:

conditioning a first electrode tip and a second electrode tip to produce a consistent roughness and a consistent surface chemical composition on each of the first electrode tip and the second electrode tip; and discharging, after the conditioning, an arc with an arc energy across an electrode gap delimited by the first electrode tip and the second electrode tip, optionally wherein the discharging includes using the controlled-energy electrical arc source of any of paragraphs A1-A24.

B2. The method of paragraph B1, wherein the conditioning includes repeatedly applying a conditioning arc between the first electrode tip and the second electrode tip until at least one of an arc parameter and a surface parameter is relatively consistent.

B2.1. The method of paragraph B2, wherein the arc parameter includes one or more of an arc energy, an arc voltage, an arc duration, and an arc power, optionally wherein a relative standard deviation in the arc parameter is less than 30%, less than 20%, less than 10%, less than 5%, less than 2%, less than 1%, less than 0.5%, less than 0.2%, or less than 0.1%.

B2.2. The method of any of paragraphs B2-B2.1, wherein the surface parameter includes the roughness of the first electrode tip and the roughness of the second electrode tip, and optionally wherein the first electrode tip and the second electrode tip each independently have an average roughness of less than 1 µm, less than 0.5 µm, less than 0.2 µm, less than 0.1 µm, less than 0.05 µm, or less than 0.01 µm.

B2.3. The method of any of paragraphs B2-B2.2, wherein the surface parameter includes the roughness of the first electrode tip and the roughness of the second electrode tip, and the surface parameter is relatively consistent when a conditioning arc does not significantly alter the roughness of the first electrode tip and the roughness of the second electrode tip.

B2.4. The method of any of paragraphs B2-B2.3, wherein the surface parameter includes the surface chemical composition of the first electrode tip and the surface chemical composition of the second electrode tip, and wherein the surface parameter is relatively consistent when a conditioning arc does not significantly alter the surface chemical composition of the first electrode tip and the surface chemical composition of the second electrode tip B2.5. The method of any of paragraphs B2-B2.4, wherein the repeatedly applying includes applying more than 100, more than 200, more than 300, more than 400, more than 500, more than 1,000, more than 2,000, more than 3,000, more than 4,000, more than 5,000, more than 6,000, more than 7,000, more than 10,000, 100-500, 200-1,000, 1,000-10,000, 2,000-5,000, about 200, about 400, about 2,000, about 3,000, about 4,000, or about 5,000 conditioning arcs.

B2.6. The method of any of paragraphs B2-B2.5, further comprising:

prior to the repeatedly applying the conditioning arc, spacing apart the first electrode tip and the second electrode tip a conditioning distance in a conditioning surrounding, wherein the conditioning surrounding is a vacuum or a gaseous medium, optionally wherein the gaseous medium includes air and/or an inert gas, and optionally wherein the conditioning distance is less than 10 mm, less than 8 mm, less than 6 mm, less than 5 mm, less than 4 mm, less than 3 mm, less than 2.5 mm, less than 2 mm, less than 1.5 mm, less than 1 mm, or less than 0.5 mm.

B2.7. The method of any of paragraphs B2-B2.6, wherein the conditioning arc has an energy of about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ, 100-250 µJ, and/or less than 1,000 µJ.

B3. The method of any of paragraphs B1-B2.7, wherein the arc energy is predefined.

B4. The method of any of paragraphs B1-B3, wherein the arc energy is about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ, 100-250 µJ, and/or less than 1,000 µJ.

B5. The method of any of paragraphs B1-B4, further comprising:
positioning the first electrode tip and the second electrode tip to delimit the electrode gap.

B6. The method of any of paragraphs B1-B5, wherein the electrode gap is delimited at less than 10 mm, less than 8 mm, less than 6 mm, less than 5 mm, less than 4 mm, less than 3 mm, less than 2.5 mm, less than 2 mm, less than 1.5 mm, less than 1 mm, less than 0.5 mm, 0.5-10 mm, or 0.5-3 mm.

B7. The method of any of paragraphs B1-B6, wherein the discharging includes discharging the arc into a combustible fluid spanning the electrode gap, optionally wherein the combustible fluid includes at least one of a liquid, a gas, a suspension of solid particles, and a suspension of liquid droplets, and optionally wherein the combustible fluid is air, and/or includes one or more of air, oxygen, hydrogen, a hydrocarbon, a fuel, a fuel vapor, an oxidant, dust, powder, and particulate.

B8. The method of any of paragraphs B1-B7, further comprising:
repeating the discharging.

B8.1. The method of paragraph B8, wherein the arcs from the repeating have an arc energy which is substantially the same, optionally wherein a relative standard deviation in arc energy is less than 30%, less than 20%, less than 10%, less than 5%, less than 2%, or less than 1%.

B9. The method of any of paragraphs B1-B8.1, further comprising:
storing, optionally after the conditioning and/or before the discharging, stored energy in a capacitor to be discharged across the electrode gap, optionally wherein the stored energy is substantially the same as the arc energy, and optionally wherein the stored energy is greater than 50%, greater than 70%, greater than 80%, greater than 90%, greater than 95%, greater than 99%, greater than 100%, or greater than 110% of the arc energy.

B10. The method of any of paragraphs B1-B9, further comprising:
applying an electrode voltage which is a high voltage across the electrode gap before the discharging, optionally wherein the electrode voltage is at least 3 kV, at least 4 kV, at least 5 kV, at least 6 kV, at least 7 kV, at least 8 kV, at least 9 kV, at least 10 kV, at least 11 kV, at least 12 kV, less than 15 kV, less than 12 kV, and/or less than 10 kV.

B10.1. The method of paragraph B10, wherein the applying includes setting the electrode voltage near a breakdown voltage of a medium spanning the electrode gap, optionally wherein the electrode voltage is about equal to, about 100 V less than, about 200 V less than, about 300 V less than, about 400 V less than, about 0-100 V less than, or about 0-300 V less than the breakdown voltage.

B11. The method of any of paragraphs B1-B10.1, further comprising:
determining whether combustion occurred in response to the discharging.

B12. The method of any of paragraphs B1-B11, wherein the discharging includes triggering the arc, optionally at a defined time and/or a defined voltage.

B12.1. The method of paragraph B12, wherein the triggering includes using an arc trigger.

B12.2. The method of any of paragraphs B12-B12.1, wherein the triggering causes the arc to occur less than 2,000 ms, less than 1,000 ms, less than 500 ms, less than 100 ms, less than 10 ms, less than 1 ms, less than 0.1 ms, less than 0.01 ms, or less than 0.01 ms after the triggering begins.

B12.3. The method of any of paragraphs B12-B12.2, wherein the triggering contributes less than 10%, less than 5%, less than 2%, less than 1%, less than 0.5%, less than 0.2%, or less than 0.1% to the arc energy.

B12.4. The method of any of paragraphs B12-B12.3, wherein the triggering contributes less than 50 µJ, less than 20 µJ, less than 10 µJ, less than 5 µJ, less than 2 µJ, less than 1 µJ, less than 0.5 µJ, less than 0.2 µJ, or less than 0.1 µJ to the arc energy.

B12.5. The method of any of paragraphs B12-B12.4, wherein the triggering includes supplying charged particles into the electrode gap and/or regulating a supply of charged particles, and optionally wherein the supplying charged particles and/or the regulating a supply of charged particles includes illuminating a target proximate to the electrode gap.

B12.5.1. The method of paragraph B12.5, wherein the target includes one or more of metal, tungsten, aluminium, stainless steel, copper, brass, nickel, silver, gold, platinum, and/or palladium.

B12.5.2. The method of any of paragraphs B12.5-B12.5.1, wherein the target is the first electrode tip and/or the second electrode tip.

B12.5.3. The method of any of paragraphs B12.5-B12.5.2, wherein the illuminating includes illuminating with a photon energy greater than or equal to a work function of the target.

B12.5.4. The method of any of paragraphs B12.5-B12.5.3, wherein the target has a work function less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, 4-6 eV, or 4-5 eV.

B12.5.5. The method of any of paragraphs B12.5-B12.5.4, wherein the illuminating includes illuminating with a photon energy greater than or equal to a photoionization energy of the target.

B12.5.6. The method of any of paragraphs B12.5-B12.5.5, wherein the target has a photoionization energy of less than about 14 eV, less than about 12 eV, less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, or 3.5-6 eV.

B12.6. The method of any of paragraphs B12-B12.5.6, wherein the illuminating includes transmitting light to the target and/or the electrode gap, wherein the light consists essentially of wavelengths of about 10-400 nm, about 80-400 nm, about 80-350 nm, about 80-280 nm, about 80-180 nm, about 200-350 nm, about 200-280 nm, or about 260-280 nm; and optionally does not include transmitting to the electrode gap light of wavelength greater than about 440 nm, greater than about 400 nm, greater than about 350 nm, greater than about 320 nm, or greater than about 280 nm.

B13. The method of any of paragraphs B1-B12.6, wherein the discharging includes discharging in the absence of corona sources.

B14. The method of any of paragraphs B1-B13, wherein the discharging includes triggering the arc in the absence of corona sources.

B15. The method of any of paragraphs B1-B14, wherein the discharging includes stabilizing an arc voltage and/or the arc energy in the absence of corona sources.

B16. The method of any of paragraphs B1-B15, wherein the discharging is used in a test system, optionally in a test system of any of paragraphs A25-A25.5, for one or more of testing a test sample, calibrating a test system, and validating a test condition.

B16.1. The method of paragraph B16, wherein the testing, the calibrating, and/or the validating includes one or more of simulating a lightning strike, initiating combustion of a fuel, applying an electrical arc, qualifying an aerospace component, qualifying an aircraft structural member, qualifying a fuel handling component, qualifying a ventilator component, and qualifying monitoring equipment.

C1. A triggered electrical arc source comprising:
a first electrode with a tip;
a second electrode with a tip, wherein the tip of the first electrode and the tip of the second electrode are spaced apart to delimit an electrode gap;
a capacitor to store a defined discharge energy at a defined discharge voltage, wherein the capacitor has a first terminal electrically connected to the first electrode and a second terminal electrically connected to the second electrode; and
a trigger source that is configured to provide charged particles proximate to the electrode gap.

C2. The triggered electrical arc source of paragraph C1, wherein the trigger source includes, is, or consists essentially of, at least one of an ion source, a plasma source, a radioactive source, an electron source, an ionizing energy source, and a light source.

C3. The triggered electrical arc source of any of paragraphs C1-C2, wherein the trigger source is configured to operate at less than 1,000 V, less than 100 V, or less than 10 V.

C4. The triggered electrical arc source of any of paragraphs C1-C3, wherein the trigger source does not include a corona generator and/or is free of a corona source.

C5. The triggered electrical arc source of any of paragraphs C1-C4, wherein the trigger source is configured to emit one or more of electrons, positrons, protons, alpha particles, ions, and ionizing radiation.

C6. The triggered electrical arc source of any of paragraphs C1-C5, wherein the trigger source is configured to be selectively enabled, selectively disabled, and/or regulated.

C7. The triggered electrical arc source of any of paragraphs C1-C6, wherein the trigger source is configured to initiate an arc with an arc energy across the electrode gap at a defined time and/or a defined voltage.

C7.1. The triggered electrical arc source of paragraph C7, wherein the trigger source is configured to contribute less than 10%, less than 5%, less than 2%, less than 1%, less than 0.5%, less than 0.2%, or less than 0.1% to the arc energy, and optionally wherein the trigger source is configured to contribute less than 50 µJ, less than 20 µJ, less than 10 µJ, less than 5 µJ, less than 2 µJ, less than 1 µJ, less than 0.5 µJ, less than 0.2 µJ, or less than 0.1 µJ to the arc energy.

C8. The triggered electrical arc source of any of paragraphs C1-C7.1, wherein the trigger source includes a delivery conduit to deliver energy and/or charged particles proximate the electrode gap, optionally wherein the delivery conduit includes one or more of an optical system, a fiber optic, a light guide, an electron multiplier, an electron accelerator, an ion accelerator, and an ion optic.

C9. The triggered electrical arc source of any of paragraphs C1-C8, wherein the trigger source includes an energy emitter and a target that emits charged particles upon absorbing energy from the energy emitter.

C9.1. The triggered electrical arc source of paragraph C9, wherein the energy emitter is configured to emit sufficient energy to ionize the target, optionally to photoionize the target.

C9.2. The triggered electrical arc source of any of paragraphs C9-C9.1, wherein the energy emitter is configured to emit sufficient energy to eject electrons from the target.

C9.3. The triggered electrical arc source of any of paragraphs C9-C9.2, wherein the target has a work function less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, 4-6 eV, or 4-5 eV.

C9.4. The triggered electrical arc source of any of paragraphs C9-C9.3, wherein the target has an ionization energy of less than about 14 eV, less than about 12 eV, less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, or 3.5-6 eV.

C9.5. The triggered electrical arc source of any of paragraphs C9-C9.4, wherein the energy emitter includes, optionally is, a light source or a UV light source; optionally wherein light emitted includes wavelengths of about 10-400 nm, about 80-400 nm, about 80-350 nm, about 80-280 nm, about 80-180 nm, about 200-350 nm, about 200-280 nm, or about 260-280 nm; and optionally wherein the source is configured to not substantially emit visible light, light of wavelength greater than about 440 nm, greater than about 400 nm, greater than about 350 nm, greater than about 320 nm, or greater than about 280 nm.

C9.5.1. The triggered electrical arc source of paragraph C9.5, wherein the energy emitter is configured to emit photons with a photon energy greater than or equal to a work function of the target.

C9.5.2. The triggered electrical arc source of any of paragraphs C9.5-C9.5.1, wherein the energy emitter is configured to emit photons with a photon energy greater than or equal to a photoionization energy of the target.

C9.6. The triggered electrical arc source of any of paragraphs C9-C9.5.2, wherein the target includes one or more of a metal, tungsten, aluminium, stainless steel, copper, brass, nickel, silver, gold, platinum, and palladium.

C9.7. The triggered electrical arc source of any of paragraphs C9-C9.6, wherein the target is proximate to the electrode gap.

C9.8. The triggered electrical arc source of any of paragraphs C9-C9.7, wherein the target includes, optionally is, one or more of a portion of the first electrode, a portion of the second electrode, the tip of the first electrode, and the tip of the second electrode.

C10. The triggered electrical arc source of any of paragraphs C1-C9.8, wherein the first electrode and/or the second electrode includes one or more of metal, tungsten, aluminium, stainless steel, copper, brass, nickel, silver, gold, platinum, and palladium.

C11. The triggered electrical arc source of any of paragraphs C1-C10, wherein the first electrode and/or the second electrode has a diameter less than 8 mm, less than 6 mm, less than 5 mm, less than 4 mm, less than 3 mm, less than 2 mm, less than 1.5 mm, less than 1 mm, greater than 1 mm, greater than 1.5 mm, greater than 2 mm, greater than 3 mm, about 1-6 mm, and/or about 1-3 mm.

C12. The triggered electrical arc source of any of paragraphs C1-C11, wherein the tip of the first electrode and/or the tip of the second electrode is rounded, convex, or substantially hemispherical.

C13. The triggered electrical arc source of any of paragraphs C1-C12, wherein the electrode gap is less than 10 mm, less than 8 mm, less than 6 mm, less than 5 mm, less than 4 mm, less than 3 mm, less than 2.5 mm, less than 2 mm, less than 1.5 mm, less than 1 mm, less than 0.5 mm, 0.5-10 mm, or 0.5-3 mm.

C14. The triggered electrical arc source of any of paragraphs C1-C13, wherein the tip of the first electrode and the tip of the second electrode are configured to produce an arc in a combustible fluid spanning the electrode gap, optionally wherein the combustible fluid includes at least one of a liquid, a gas, a suspension of solid particles, and a suspension of liquid droplets, and optionally wherein the combustible fluid is air, and/or includes one or more of air, oxygen, hydrogen, a hydrocarbon, a fuel, a fuel vapor, an oxidant, dust, powder, and particulate.

C14.1. The triggered electrical arc source of paragraph C14, wherein the arc has an arc energy substantially the same as the defined discharge energy, optionally wherein the defined discharge energy is greater than 50%, greater than 70%, greater than 80%, greater than 90%, greater than 95%, greater than 99%, greater than 100%, or greater than 110% of the arc energy.

C15. The triggered electrical arc source of any of paragraphs C1-C14.1, wherein the tip of the first electrode and the tip of the second electrode are configured to produce a series of arcs with substantially the same arc energies, optionally wherein a relative standard deviation in arc energy is less than 30%, less than 20%, less than 10%, less than 5%, less than 2%, or less than 1%.

C16. The triggered electrical arc source of any of paragraphs C1-C15, wherein the capacitor is a variable capacitor, optionally wherein the capacitor is an automatically controlled variable capacitor or is a manually controlled variable capacitor.

C17. The triggered electrical arc source of any of paragraphs C1-C16, wherein the capacitor is about 1 pF, about 2 pF, about 4 pF, about 6 pF, about 8 pF, about 10 pF, about 12 pF, about 15 pF, about 20 pF, about 25 pF, about 30 pF, about 50 pF, about 2-10 pF, about 2-15 pF, about 4-20 pF, less than 50 pF, less than 20 pF, or less than 10 pF.

C18. The triggered electrical arc source of any of paragraphs C1-C17, wherein the triggered electrical arc source has a parasitic capacitance of less than 2 pF, less than 1 pF, less than 0.5 pF, less than 0.2 pF, or less than 0.1 pF.

C19. The triggered electrical arc source of any of paragraphs C1-C18, wherein the triggered electrical arc source has a net capacitance of about 1 pF, about 2 pF, about 4 pF, about 6 pF, about 8 pF, about 10 pF, about 12 pF, about 15 pF, about 20 pF, about 25 pF, about 30 pF, about 50 pF, about 2-10 pF, about 2-15 pF, about 4-20 pF, less than 50 pF, less than 20 pF, or less than 10 pF.

C20. The triggered electrical arc source of any of paragraphs C1-C19, wherein the defined discharge energy is about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ 100-250 µJ, and/or less than 1,000 µJ.

C21. The triggered electrical arc source of any of paragraphs C1-C20, wherein the defined discharge voltage is at least 3 kV, at least 4 kV, at least 5 kV, at least 6 kV, at least 7 kV, at least 8 kV, at least 9 kV, at least 10 kV, at least 11 kV, at least 12 kV, 6-8 kV, less than 15 kV, less than 12 kV, and/or less than 10 kV.

C22. The triggered electrical arc source of any of paragraphs C1-C21, further comprising:

a housing enclosing the capacitor and a first lead to the first electrode and a second lead to the second electrode, optionally wherein the housing is filled with a fill material with a high dielectric strength, optionally wherein the high dielectric strength is greater than 3 MV/m, greater than 4 MV/m, greater than 5 MV/m, greater than 7 MV/m, greater than 10 MV/m, greater than 15 MV/m, greater than 20 MV/m, about 10 MV/m, about 15 MV/m, or about 20 MV/m.

C22.1. The triggered electrical arc source of paragraph C22, wherein the housing is one or more of electrically insulating, non-absorbent, non-hygroscopic, inert, non-reactive, non-reactive with hydrocarbon fuels, and non-flammable.

C22.2. The triggered electrical arc source of any of paragraphs C22-C22.1, wherein the housing includes, or is composed of, a housing material with a low dielectric constant, optionally wherein the dielectric constant is less than about 10, less than about 5, less than about 3, or less than about 2.

C22.3. The triggered electrical arc source of any of paragraphs C22-C22.2, wherein the housing includes one or more of PTFE, fluoropolymer, PEEK, polyoxymethylene, hard rubber, phenolic resin, polyamide, ceramic, and glass.

C22.4. The triggered electrical arc source of any of paragraphs C22-C22.3, wherein the housing has a volume less than 1,000 cm$^3$, less than 500 cm$^3$, less than 200 cm$^3$, or less than 100 cm$^3$.

C22.5. The triggered electrical arc source of any of paragraphs C22-C22.4, wherein the fill material includes one or more of insulating oil, mineral oil, silicone oil, perfluorinated fluid, silicone resin, polyurethane, epoxy, and potting compound.

C22.6. The triggered electrical arc source of any of paragraphs C22-C22.5, wherein the trigger source is operatively coupled to the housing, and optionally, when dependent from paragraph C8, wherein the delivery conduit is operatively coupled to the housing.

C23. The triggered electrical arc source of any of paragraphs C1-C22.6, further comprising:

an isolation resistor in series with the capacitor, optionally wherein the isolation resistor is greater than 1 GΩ, greater than 10 GΩ, greater than 50 GΩ, greater than 100 GΩ, greater than 150 GΩ, greater than 200 GΩ, greater than 300 GΩ, or greater than 500 GΩ.

C24. The triggered electrical arc source of any of paragraphs C1-C23, further comprising:

a power supply to supply energy to the capacitor, optionally wherein the power supply is configured to apply the defined discharge voltage across the capacitor.

C24.1. The triggered electrical arc source of paragraph C24, wherein the power supply is configured to apply an adjustable voltage across the capacitor, optionally wherein the adjustable voltage is between 0-10 kV, 0-8 kV, or 6-8 kV.

C25. The triggered electrical arc source of any of paragraphs C1-C24.1, further comprising:

an energy meter to measure the electrical energy discharged through the electrode gap, optionally wherein the energy meter is, or includes, an electrostatic voltmeter, a current sensor, and/or a Rogowski coil.

C26. The triggered electrical arc source of any of paragraphs C1-C25, further comprising:

at least two flanges to allow a flame kernel to grow, wherein a flange is proximate the first electrode and another flange is proximate the second electrode, optionally wherein the at least two flanges delimit a flange gap that includes the electrode gap.

C26.1. The triggered electrical arc source of paragraph C26, wherein the at least two flanges are one or more of electrically insulating, non-absorbent, non-hygroscopic, inert, non-reactive, non-reactive with hydrocarbon fuels, and non-flammable.

C26.2. The triggered electrical arc source of any of paragraphs C26-C26.1, wherein the at least two flanges include, or are composed of, a flange material with a low dielectric constant, optionally wherein the dielectric constant is less than about 10, less than about 5, or less than about 3.

C26.3. The triggered electrical arc source of any of paragraphs C26-C26.2, wherein each flange independently includes one or more of PTFE, fluoropolymer, PEEK, polyoxymethylene, hard rubber, phenolic resin, polyamide, ceramic, and glass.

C26.4. The triggered electrical arc source of any of paragraphs C26-C26.3, wherein a maximum lateral dimension of one or more of the at least two flanges is less than 50 mm, less than 25 mm, less than 20 mm, less than 15 mm, less than 12 mm, less than 10 mm, less than 8 mm, less than 6 mm, less than 5 mm, 5-50 mm, 6-25 mm, 6-20 mm, 6-12 mm, greater than 5 mm, greater than 6 mm, greater than 8 mm, greater than 10 mm, greater than 12 mm, and/or greater than 20 mm.

C26.5. The triggered electrical arc source of any of paragraphs C26-C26.4, wherein the flange gap is a substantially planar parallel gap, and optionally is greater than 1 mm, greater than 2 mm, greater than 3 mm, greater than 4 mm, greater than 5 mm, greater than 6 mm, greater than 7 mm, greater than 8 mm, greater than 10 mm, greater than 12 mm, 2-10 mm, 3-10 mm, 6-12 mm, less than 15 mm, less than 12 mm, less than 10 mm, less than 8 mm, and/or less than 6 mm.

C26.6. The triggered electrical arc source of any of paragraphs C26-C26.5, when dependent from paragraph C8, wherein the delivery conduit is operatively coupled to at least one of the at least two flanges.

C27. The triggered electrical arc source of any of paragraphs C1-C26.6, further comprising:
a controller programmed to control one or more of the storage of the defined discharge energy in the capacitor, the discharge of the defined discharge energy in an arc across the electrode gap, the setting of the defined discharge voltage, and the provision of charged particles from the trigger source.

C27.1. The triggered electrical arc source of paragraph C27, wherein the controller is configured to set the defined discharge voltage to a set voltage near a breakdown voltage of a medium within the electrode gap, optionally wherein the set voltage is about equal to, about 100 V less than, about 200 V less than, about 300 V less than, about 400 V less than, about 0-100 V less than, or about 0-300 V less than the breakdown voltage.

C27.2. The triggered electrical arc source of any of paragraphs C27-C27.1, wherein the controller is configured to control the provision of charged particles, and optionally configured to enable the provision of charged particles, after setting of the defined discharge voltage.

C28. A test system, optionally an aerospace component test system, comprising:
a test chamber;
the triggered electrical arc source of any of paragraphs C1-C27.2, at least partially enclosed by the test chamber; and
a test sample at least partially enclosed by the test chamber.

C28.1. The test system of paragraph C28, further comprising:

an energy source to apply energy to the test sample, optionally wherein the energy source includes, optionally is, one or more of a lightning simulator, a heater, and an exposed electrical arc.

C28.2. The test system of any of paragraphs C28-C28.1, further comprising:
a combustible fluid enclosed by the test chamber, optionally wherein the combustible fluid includes at least one of a liquid, a gas, a suspension of solid particles, and a suspension of liquid droplets, and optionally wherein the combustible fluid is air, and/or includes one or more of air, oxygen, hydrogen, a hydrocarbon, a fuel, a fuel vapor, an oxidant, dust, powder, and particulate.

C28.3. The test system of any of paragraphs C28-C28.2, further comprising:
monitoring equipment, optionally wherein the monitoring equipment includes, optionally is, one or more of a pressure transducer, a pressure indicator, a microphone, a heat transducer, a heat indicator, a photodetector, a camera, an electrical power meter, an electrostatic voltmeter, an oscilloscope, a current sensor, and a Rogowski coil.

C28.4. The test system of any of paragraphs C28-C28.3, wherein the test sample is at least partially solid, liquid, and/or gaseous.

C28.5. The test system of any of paragraphs C28-C28.4, wherein the test sample includes, optionally is, a fuel mixture, an aerospace component, an aircraft structural member, a fuel handling component, a ventilator component, and/or equipment.

C29. A fuel mixture calibrated using the triggered electrical arc source of any of paragraphs C1-C27.2 and/or the test system of any of paragraphs C28-C28.5.

D1. A method of generating a controlled electrical arc, comprising:
applying an electrode voltage across an electrode gap delimited by a first electrode tip and a second electrode tip; and
triggering an arc with an arc energy across the electrode gap by supplying charged particles into the electrode gap, optionally wherein the triggering includes using the controlled-energy electrical arc source of any of paragraphs A1-A24 and/or the triggered electrical arc source of any of paragraphs C1-C27.2.

D2. The method of paragraph D1, wherein the applying includes setting the electrode voltage to a high voltage, optionally wherein the high voltage is at least 3 kV, at least 4 kV, at least 5 kV, at least 6 kV, at least 7 kV, at least 8 kV, at least 9 kV, at least 10 kV, at least 11 kV, at least 12 kV, less than 15 kV, less than 12 kV, and/or less than 10 kV.

D3. The method of any of paragraphs D1-D2, wherein the applying includes setting the electrode voltage near a breakdown voltage of a medium spanning the electrode gap, optionally wherein the electrode voltage is about equal to, about 100 V less than, about 200 V less than, about 300 V less than, about 400 V less than, about 0-100 V less than, or about 0-300 V less than the breakdown voltage.

D4. The method of any of paragraphs D1-D3, wherein the triggering includes triggering the arc at a defined time and/or a defined voltage, optionally wherein the triggering includes regulating a supply of charged particles.

D5. The method of any of paragraphs D1-D4, wherein the triggering causes the arc to occur less than 2,000 ms, less than 1,000 ms, less than 500 ms, less than 100 ms, less than 10 ms, less than 1 ms, less than 0.1 ms, less than 0.01 ms, or less than 0.01 ms after the triggering begins.

D6. The method of any of paragraphs D1-D5, wherein the triggering contributes less than 10%, less than 5%, less than 2%, less than 1%, less than 0.5%, less than 0.2%, or less than 0.1% to the arc energy.

D7. The method of any of paragraphs D1-D6, wherein the triggering contributes less than 50 µJ, less than 20 µJ, less than 10 µJ, less than 5 µJ, less than 2 µJ, less than 1 µJ, less than 0.5 µJ, less than 0.2 µJ, or less than 0.1 µJ to the arc energy.

D8. The method of any of paragraphs D1-D7, wherein the supplying charged particles includes illuminating a target proximate to the electrode gap.

D8.1. The method of paragraph D8, wherein the target includes one or more of metal, tungsten, aluminium, stainless steel, copper, brass, nickel, silver, gold, platinum, and/or palladium.

D8.2. The method of any of paragraphs D8-D8.1, wherein the target is the first electrode tip and/or the second electrode tip.

D8.3. The method of any of paragraphs D8-D8.2, wherein the illuminating includes illuminating with a photon energy greater than or equal to a work function of the target.

D8.4. The method of any of paragraphs D8-D8.3, wherein the target has a work function less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, 4-6 eV, or 4-5 eV.

D8.5. The method of any of paragraphs D8-D8.4, wherein the illuminating includes illuminating with a photon energy greater than or equal to a photoionization energy of the target.

D8.6. The method of any of paragraphs D8-D8.5, wherein the target has an photoionization energy of less than about 14 eV, less than about 12 eV, less than about 10 eV, less than about 6 eV, less than about 5 eV, less than about 4.5 eV, less than about 4 eV, less than about 3.5 eV, greater than about 3 eV, greater than about 3.5 eV, greater than about 4 eV, greater than about 4.5 eV, 3.5-10 eV, or 3.5-6 eV.

D8.7. The method of any of paragraphs D8-D8.6, wherein the illuminating includes transmitting light to the target and/or the electrode gap, wherein the light consists essentially of wavelengths of about 10-400 nm, about 80-400 nm, about 80-350 nm, about 80-280 nm, about 80-180 nm, about 200-350 nm, about 200-280 nm, or about 260-280 nm; and optionally does not include transmitting to the electrode gap light of wavelength greater than about 440 nm, greater than about 400 nm, greater than about 350 nm, greater than about 320 nm, or greater than about 280 nm.

D9. The method of any of paragraphs D1-D8.7, wherein the triggering includes triggering the arc in the absence of corona sources.

D10. The method of any of paragraphs D1-D9, wherein the triggering includes discharging in the absence of corona sources, optionally wherein the discharging includes stabilizing an arc voltage and/or the arc energy in the absence of corona sources.

D11. The method of any of paragraphs D1-D10, wherein the arc energy is predefined.

D12. The method of any of paragraphs D1-D11, wherein the arc energy is about 10 µJ, about 20 µJ, about 50 µJ, about 80 µJ, about 100 µJ, about 150 µJ, about 200 µJ, about 250 µJ, about 300 µJ, about 400 µJ, about 500 µJ, about 1,000 µJ, 50-500 µJ, 100-250 µJ, and/or less than 1,000 µJ.

D13. The method of any of paragraphs D1-D12, further comprising:
positioning the first electrode tip and the second electrode tip to delimit the electrode gap.

D14. The method of any of paragraphs D1-D13, wherein the electrode gap is delimited at less than 10 mm, less than 8 mm, less than 6 mm, less than 5 mm, less than 4 mm, less than 3 mm, less than 2.5 mm, less than 2 mm, less than 1.5 mm, less than 1 mm, less than 0.5 mm, 0.5-10 mm, or 0.5-3 mm.

D15. The method of any of paragraphs D1-D14, wherein the triggering includes discharging the arc into a combustible fluid spanning the electrode gap, optionally wherein the combustible fluid includes at least one of a liquid, a gas, a suspension of solid particles, and a suspension of liquid droplets, and optionally wherein the combustible fluid is air, and/or includes one or more of air, oxygen, hydrogen, a hydrocarbon, a fuel, a fuel vapor, an oxidant, dust, powder, and particulate.

D16. The method of any of paragraphs D1-D15, further comprising:
repeating the triggering.

D16.1. The method of paragraph D16, wherein the arc energy of the arcs from the repeating is substantially the same, optionally wherein a relative standard deviation in arc energy is less than 30%, less than 20%, less than 10%, less than 5%, less than 2%, or less than 1%.

D17. The method of any of paragraphs D1-D16.1, further comprising:
storing, optionally before the triggering, stored energy in a capacitor to be discharged across the electrode gap, optionally wherein the stored energy is substantially the same as the arc energy, and optionally wherein the stored energy is greater than 50%, greater than 70%, greater than 80%, greater than 90%, greater than 95%, greater than 99%, greater than 100%, or greater than 110% of the arc energy.

D18. The method of any of paragraphs D1-D17, further comprising:
determining whether combustion occurred in response to the triggering.

D19. The method of any of paragraphs D1-D18, wherein the triggering includes using a test system, optionally a test system of any of paragraphs A25-A25.5 and/or a test system of any of paragraphs C28-C28.5, for one or more of testing a test sample, calibrating a test system, and validating a test condition.

D19.1. The method of paragraph D19, wherein the testing, the calibrating, and/or the validating includes one or more of simulating a lightning strike, initiating combustion of a fuel, applying an electrical arc, qualifying an aerospace component, qualifying an aircraft structural member, qualifying a fuel handling component, qualifying a ventilator component, and qualifying monitoring equipment.

As used herein, the terms "selective" and "selectively," when modifying an action, movement, configuration, or other activity of one or more components or characteristics of an apparatus, mean that the specific action, movement, configuration, or other activity is a direct or indirect result of user manipulation of an aspect of, or one or more components of, the apparatus.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

The invention claimed is:

1. A method of generating a controlled electrical arc in a component test system, comprising:
    applying an electrode voltage across an electrode gap delimited by a first electrode tip and a second electrode tip, wherein the electrode voltage is about 0-300 V less than a breakdown voltage of a medium spanning the electrode gap;
    storing stored energy in a capacitor to be discharged across the electrode gap; and
    triggering an arc with an arc energy across the electrode gap, wherein the triggering includes illuminating the first electrode tip with UV light to emit electrons from the first electrode tip and to trigger the arc with the electrons, wherein the UV light has a photon energy that is greater than or equal to a work function of the first electrode tip, and wherein the arc energy is substantially the same as the stored energy.

2. A method of generating a controlled electrical arc in a component test system, comprising:
    applying an electrode voltage across an electrode gap delimited by a first electrode tip and a second electrode tip; and
    triggering an arc with an arc energy across the electrode gap, wherein the triggering includes illuminating a metal target proximate to the electrode gap, to supply charged particles into the electrode gap and to trigger the arc with the charged particles.

3. The method of claim 2, wherein the applying includes setting the electrode voltage about 0-300 V less than a breakdown voltage of a medium spanning the electrode gap.

4. The method of claim 2, wherein the triggering includes regulating electrons within the electrode gap.

5. The method of claim 2, wherein the triggering includes causing the arc to occur less than 200 ms after the illuminating begins.

6. The method of claim 2, wherein the triggering contributes less than 1% to the arc energy.

7. The method of claim 2, wherein the triggering contributes less than 2 µJ to the arc energy.

8. The method of claim 2, wherein the illuminating includes illuminating the first electrode tip as the metal target.

9. The method of claim 2, wherein the illuminating includes illuminating with a photon energy greater than or equal to a work function of the metal target.

10. The method of claim 2, wherein the illuminating includes transmitting light to the metal target that consists essentially of UV light.

11. The method of claim 10, where the light includes wavelengths of about 200-350 nm.

12. The method of claim 2, wherein the triggering includes triggering in the absence of corona sources.

13. The method of claim 2, further comprising storing stored energy to be discharged across the electrode gap, wherein the stored energy is predefined between 50-500 µJ, and wherein the arc energy includes the stored energy and is substantially the same as the stored energy.

14. The method of claim 2, wherein the illuminating includes illuminating through a fiber optic.

15. The method of claim 14, wherein the fiber optic is coupled to a flange proximate to the second electrode tip.

16. A triggered electrical arc source comprising:
    a first electrode with a tip;
    a second electrode with a tip, wherein the tip of the first electrode and the tip of the second electrode are spaced apart to delimit an electrode gap;
    a capacitor to store a defined discharge energy at a defined discharge voltage, wherein the capacitor has a first terminal electrically connected to the first electrode and a second terminal electrically connected to the second electrode;
    a light source to illuminate a metal target proximate to the electrode gap and to supply electrons into the electrode gap, wherein the light source is configured to emit photons with a photon energy greater than or equal to a work function of the metal target;
    at least two flanges to allow a flame kernel to grow, wherein a flange is proximate the first electrode and another flange is proximate the second electrode, wherein the at least two flanges delimit a flange gap that includes the electrode gap; and
    a housing enclosing the capacitor and a first lead to the first electrode and a second lead to the second electrode, wherein the light source is operatively coupled to the housing.

17. The triggered electrical arc source of claim 16, wherein the light source is configured to emit essentially UV light.

18. The triggered electrical arc source of claim 16, wherein the light source is configured to emit wavelengths of about 200-350 nm.

19. The triggered electrical arc source of claim 16, wherein each flange has a dielectric constant of less than about 10.

20. The triggered electrical arc source of claim 16, wherein the metal target includes a portion of the first electrode.

21. The triggered electrical arc source of claim 16, wherein the light source includes a fiber optic.

22. An aerospace component test system comprising:
    a test chamber;
    the triggered electrical arc source of claim 16, at least partially enclosed by the test chamber; and
    a test sample at least partially enclosed by the test chamber.

* * * * *